United States Patent [19]
Yoshimura et al.

[11] Patent Number: 5,414,356
[45] Date of Patent: May 9, 1995

[54] FLUXMETER INCLUDING SQUID AND PICKUP COIL WITH FLUX GUIDING CORE AND METHOD FOR SENSING DEGREE OF DETERIORATION OF AN OBJECT

[75] Inventors: Toshihiko Yoshimura, Ibaraki; Tasuku Shimizu, Hitachi; Yuichi Ishikawa, Mito; Masahiro Otaka, Hitachi, all of Japan; Yuko Koguchi, Solwez, Zambia; Kunio Enomoto, Ibaraki, Japan; Kunio Hasegawa, Katsuta, Japan; Makoto Hayashi; Kazuo Takaku, both of Hitachi, Japan

[73] Assignee: Hitachi, Ltd., Tokyo, Japan

[21] Appl. No.: 738,240

[22] Filed: Jul. 30, 1991

Related U.S. Application Data

[63] Continuation-in-part of Ser. No. 333,276, Apr. 5, 1989, abandoned, and a continuation-in-part of Ser. No. 247,414, Sep. 21, 1988, Pat. No. 5,059,903.

[30] Foreign Application Priority Data

| Sep. 21, 1987 | [JP] | Japan | 62-234828 |
| Nov. 4, 1987 | [JP] | Japan | 62-277445 |
| Dec. 4, 1987 | [JP] | Japan | 62-305656 |
| Apr. 6, 1988 | [JP] | Japan | 63-82966 |

[51] Int. Cl.$^6$ ............... G01R 33/12; G01R 33/035; G01N 27/72; H01F 17/04
[52] U.S. Cl. ................... 324/239; 324/223; 324/227; 324/240; 324/248; 336/200; 336/221
[58] Field of Search ........ 324/201, 209, 223, 234–243, 324/248, 258, 260; 336/200, 221, 232; 505/843, 846

[56] References Cited

U.S. PATENT DOCUMENTS

| 3,861,206 | 1/1975 | Kawafune et al. | 324/209 |
| 4,016,519 | 4/1977 | Haas | 336/200 |
| 4,223,360 | 9/1980 | Sansom et al. | 336/232 X |
| 4,588,947 | 5/1986 | Ketchen | 324/248 X |
| 4,613,817 | 9/1986 | Hoenig | 324/248 |
| 4,649,755 | 3/1987 | Volz | 336/200X |
| 4,716,773 | 1/1988 | Nonomura et al. | 324/209 X |
| 4,875,010 | 10/1989 | Yokosawa et al. | 324/248 |
| 4,931,730 | 6/1990 | Olsen et al. | 324/209 |

FOREIGN PATENT DOCUMENTS

| 14512 | 1/1983 | Japan |  |
| 169070 | 10/1983 | Japan | 324/248 |

Primary Examiner—Gerard R. Strecker
Attorney, Agent, or Firm—Antonelli, Terry, Stout & Kraus

[57] ABSTRACT

A fluxmeter includes an application unit for applying a magnetic field, a superconducting quantum interference element and a flux transmitting circuit. The flux transmitting circuit includes a pickup coil formed of a superconducting print coil and a core for the pickup coil. The core is formed of a soft magnetic material. The core serves to suppress the leakage of magnetic flux to magnetically couple the pickup coil and the superconducting quantum interference element efficiently to improve the sensitivity and resolution of the fluxmeter. The pickup coil may be manufactured by photolithography, sputtering, laser beam deposition, MBE deposition, MOCVD or spray pyrolysis.

38 Claims, 31 Drawing Sheets

F I G. 2
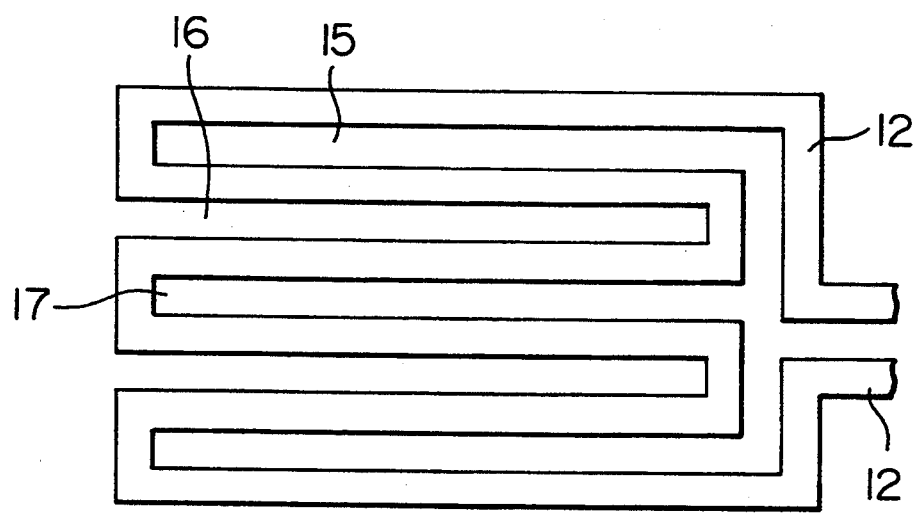
F I G. 3
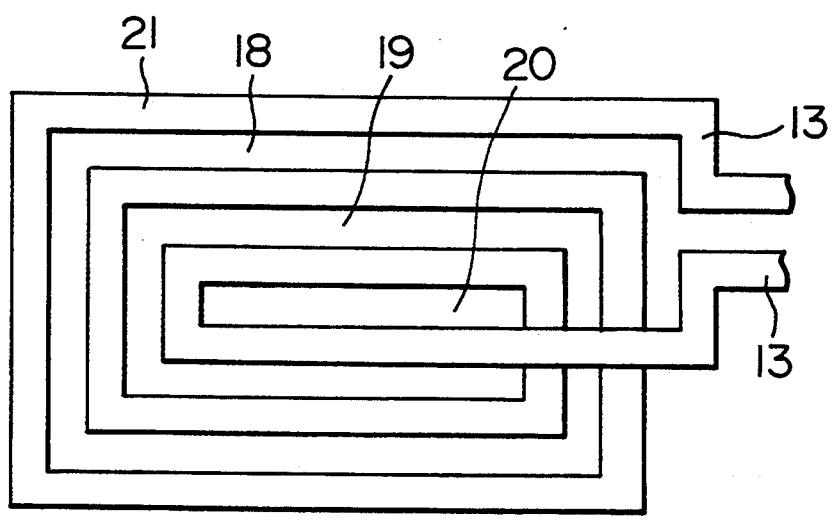

F I G. 7
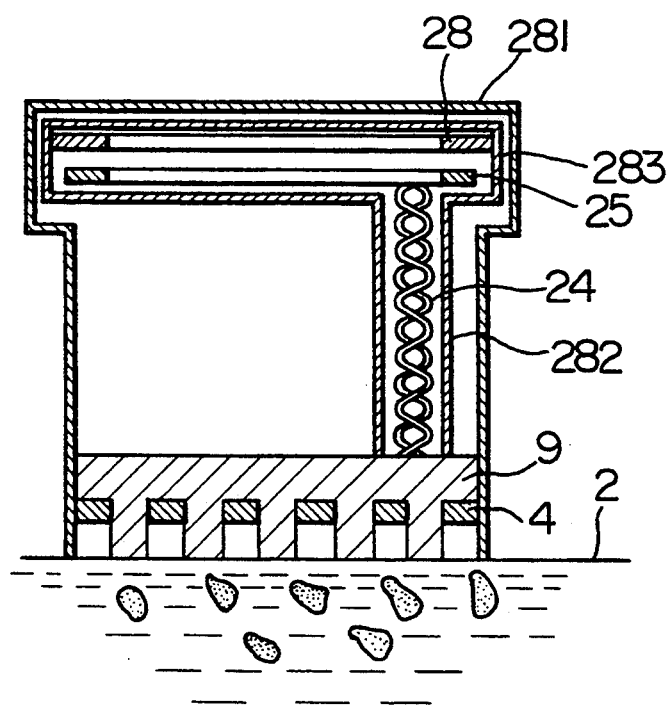

PRESENT INVENTION

F I G. 14
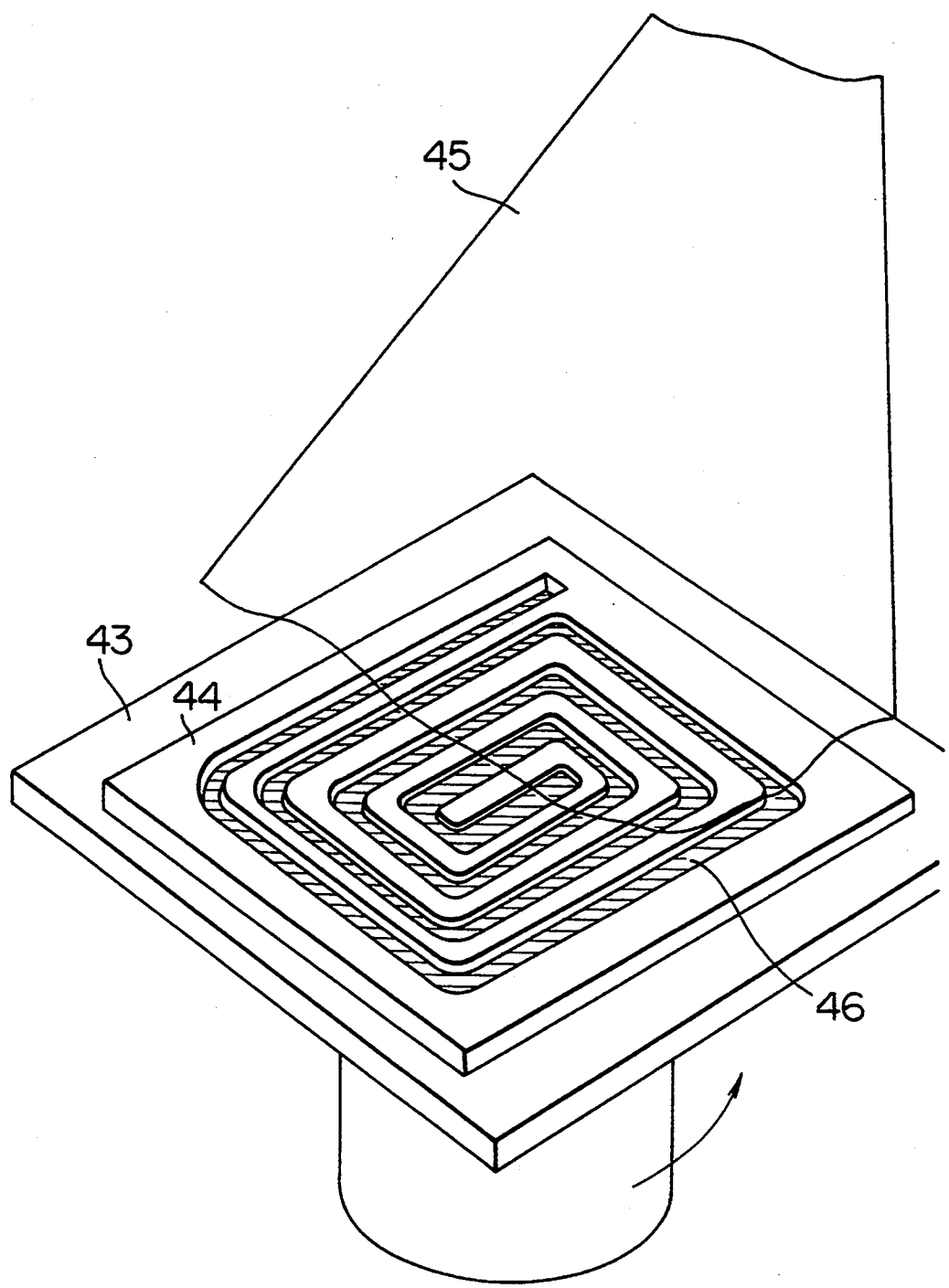

PREPARE PRINT COIL NEGATIVE IMAGE

DEPOSIT SUPERCONDUCTING THIN FILM

REMOVE NEGATIVE IMAGE FORMING SUBSTANCE

DEPOSIT SUPERCONDUCTING THIN FILM

FORM PRINT COIL PATTERN WITH PHOTOSENSITIVE RESIN

ETCH AWAY NEGATIVE PATTERN CHEMICALLY

REMOVE PHOTOSENSITIVE RESIN WITH SOLVENT

F I G. 20
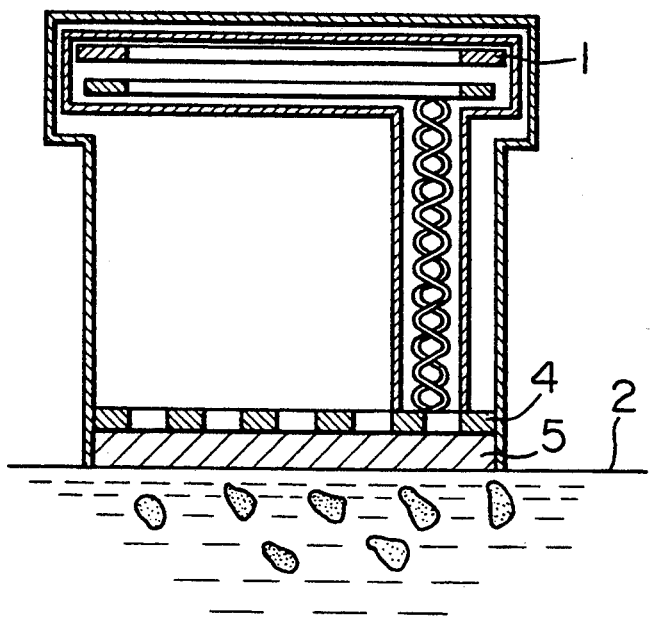
F I G. 21
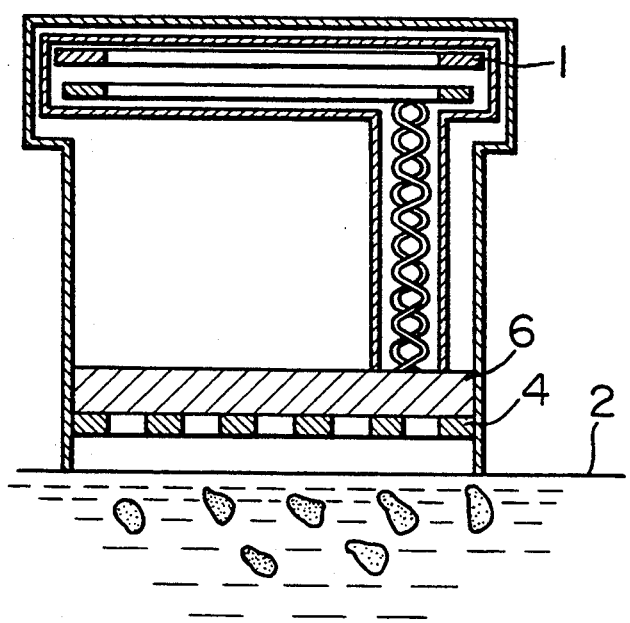

F I G. 27
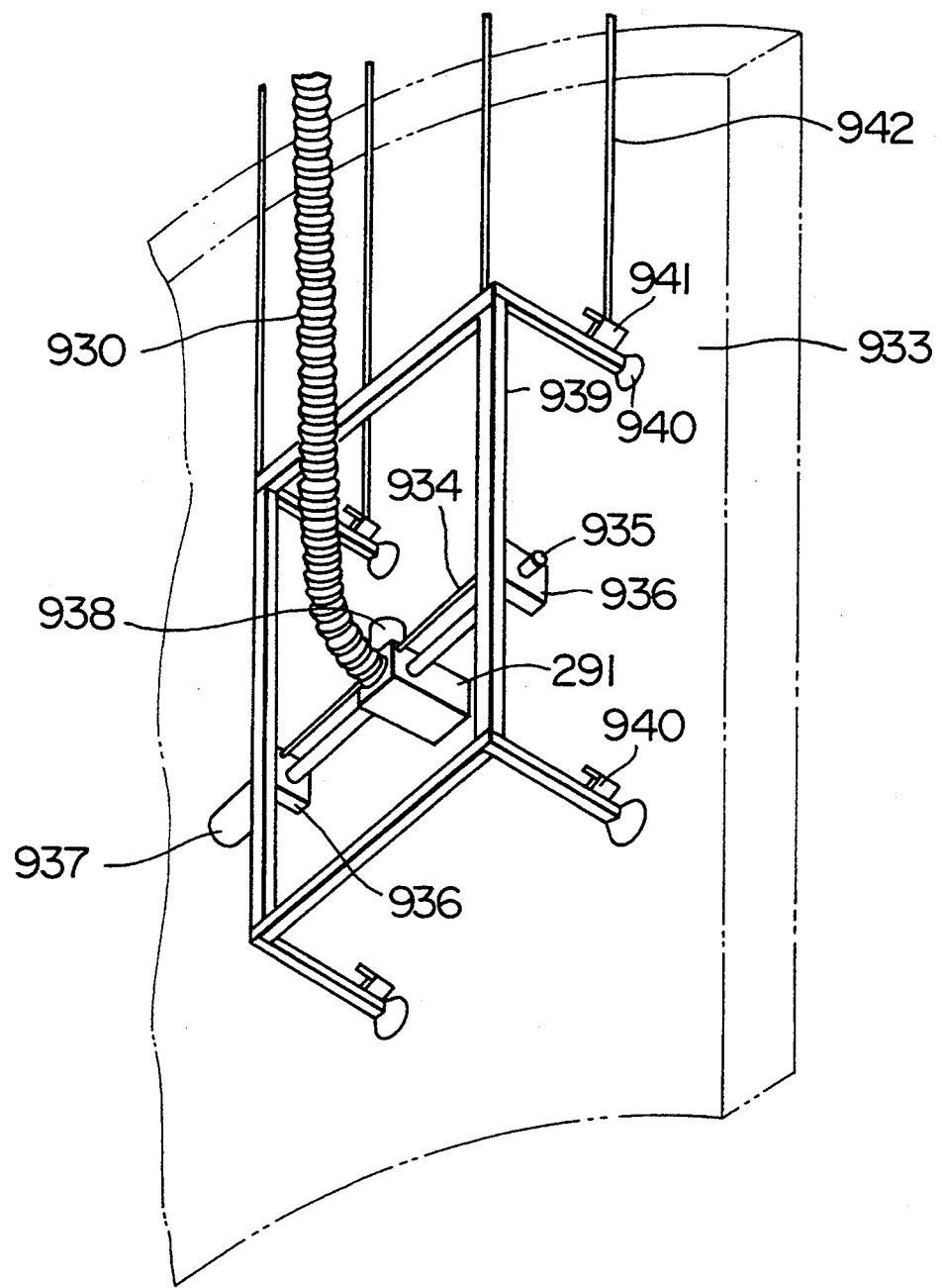

F I G. 28
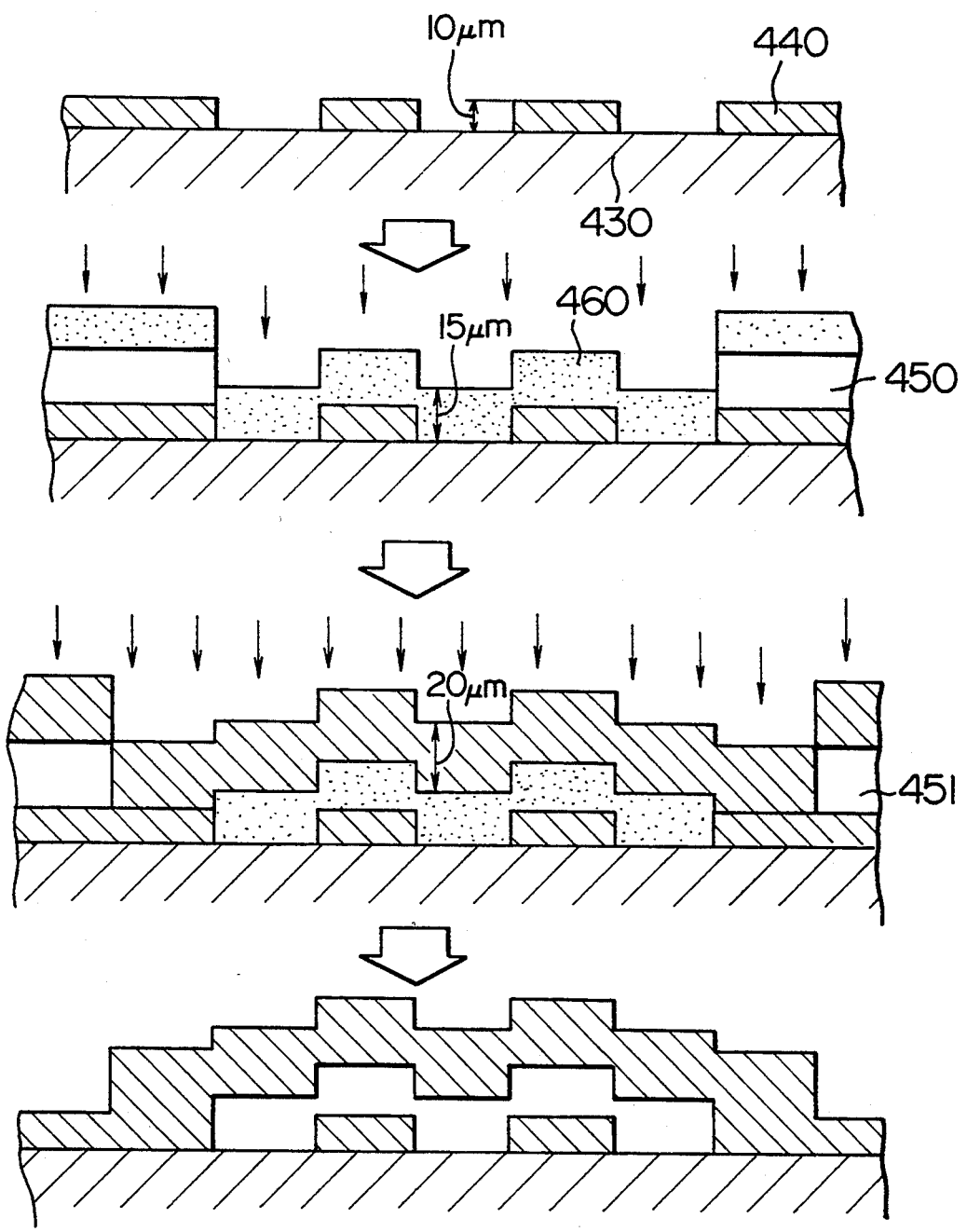

F I G. 31
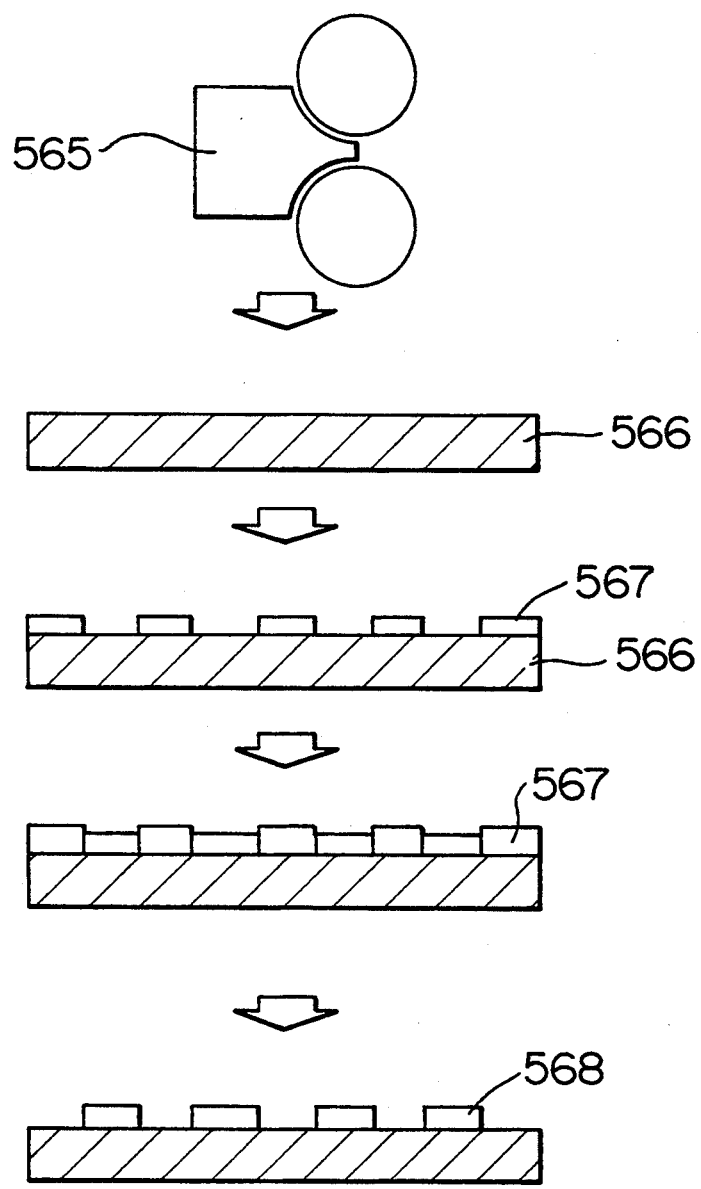

F I G. 33
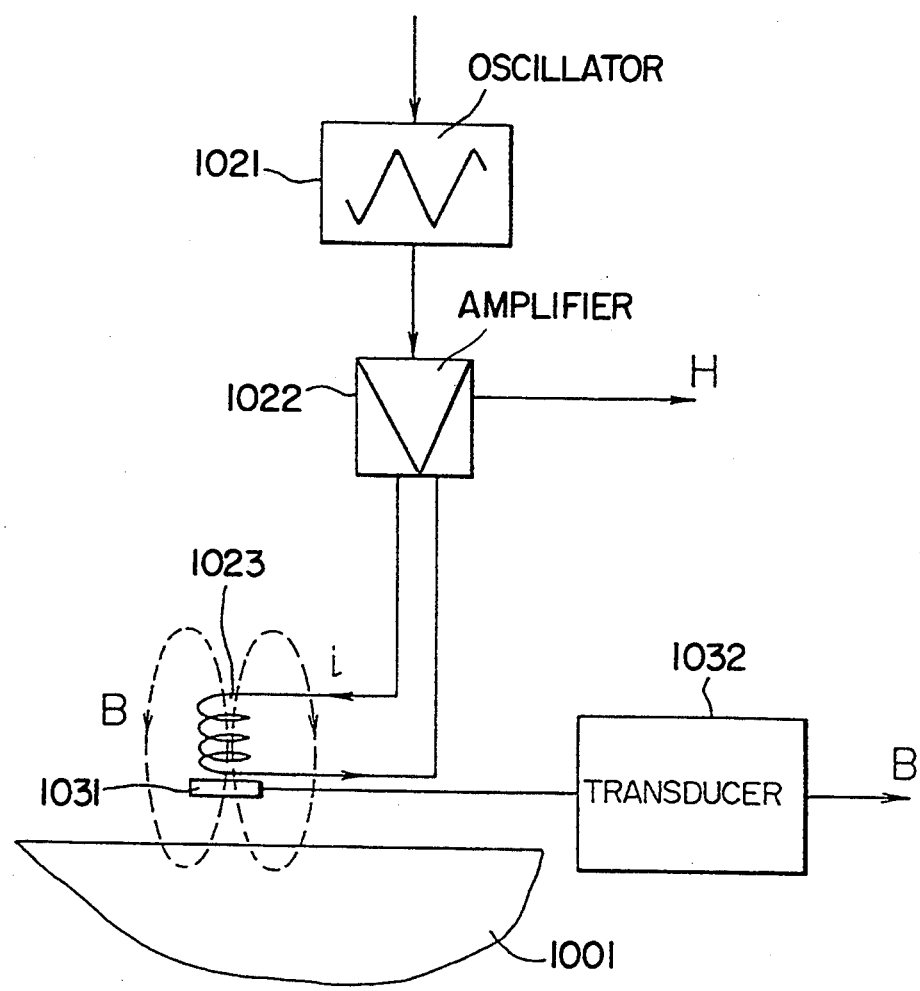

F I G. 34
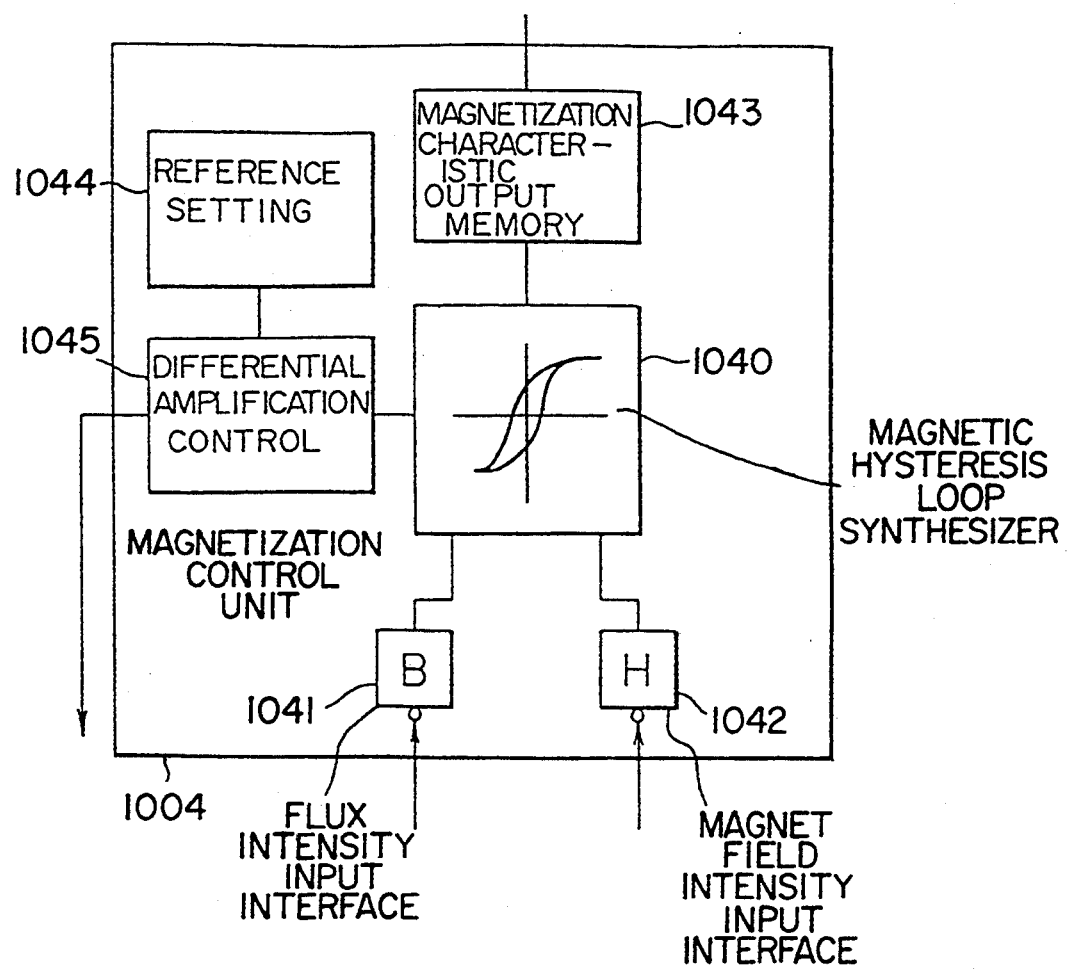

F I G. 35
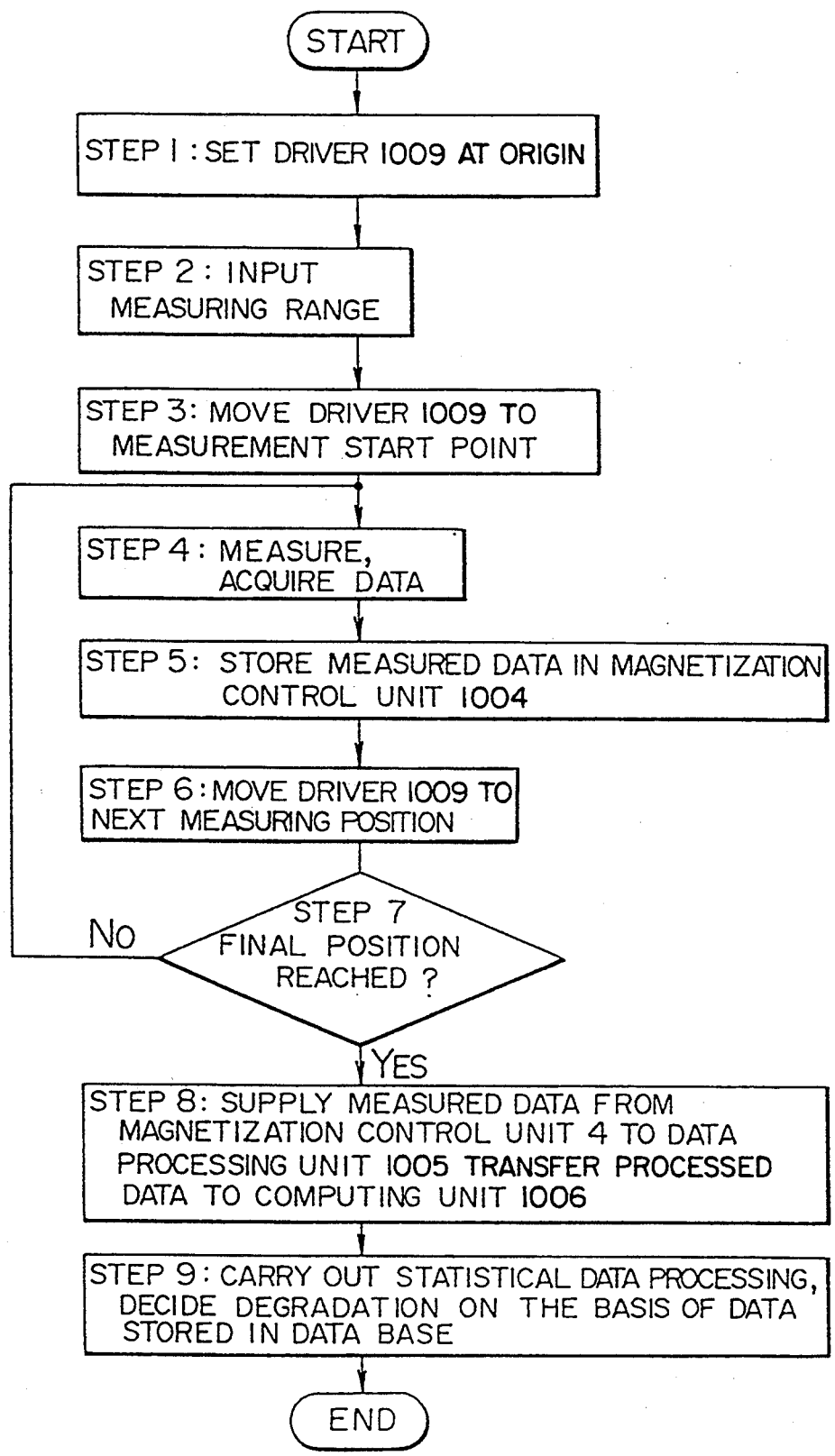

$P = 748 \times (5.7 + \log t) \times 10^{-}$

F I G. 39
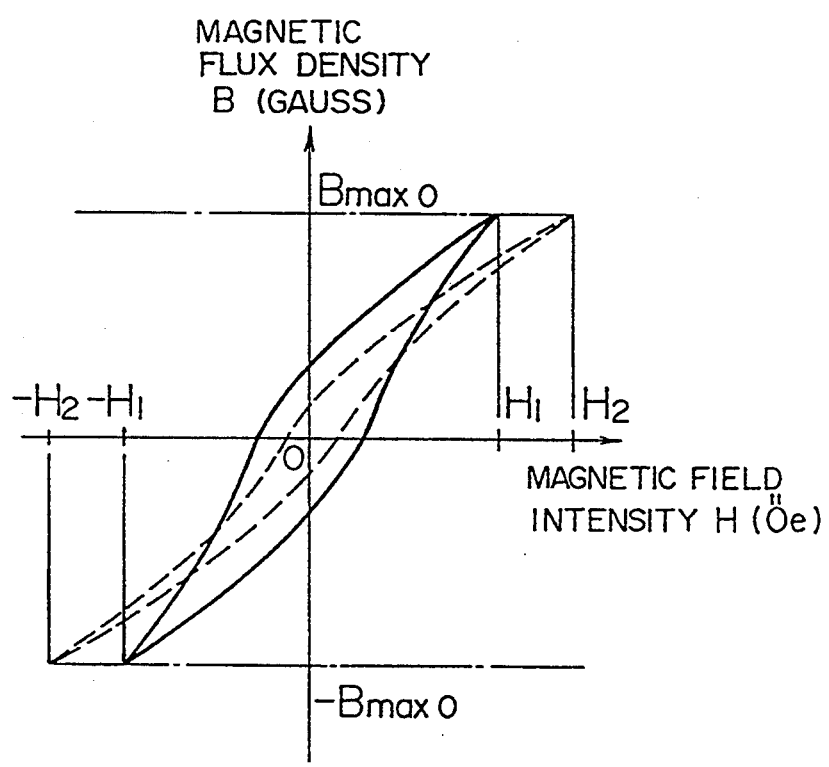

FLUXMETER INCLUDING SQUID AND PICKUP COIL WITH FLUX GUIDING CORE AND METHOD FOR SENSING DEGREE OF DETERIORATION OF AN OBJECT

CROSS REFERENCE TO RELATED APPLICATION

The present application is a continuation-in-part of application Ser. No. 333,276, filed Apr. 5, 1989, now abandoned, and is a continuation-in-part application of application Ser. No. 247,414, filed Sep. 21, 1988, now U.S. Pat. No. 5,059,903, the subject matter of which is incorporated herein by reference.

BACKGROUND OF THE INVENTION

The present invention relates to fluxmeters using a superconducting quantum interference device, and more particularly to pickup coils (probe coils) and their cores in the fluxmeters suitable for detecting long-term embrittlement (concerning thermal aging) of a metal material such as ferrite stainless steel used under high temperature environments such as chemical plants and atomic power plants.

Japanese Patent Publication JP-A-62-277704 discloses a method of manufacturing superconducting sheet coils which exhibit a high critical current characteristic in a high magnetic field used for a nuclear fusion toroidal magnet, a particle accelerator magnet, a superconducting generator magnet, etc., but which do not exhibit such characteristics in a low magnetic field used, for example, in the diagnosis of the deterioration of ferrite stainless steel.

Japanese Patent Publication JP-A-61-28859 discloses a method of detecting the degree of long-term embrittlement damage of a ferrite stainless steel member used in an actual plant. In this method, a change in the quantity of ferrite in the actual plant Member after long term use under high-temperature conditions is magnetically measured using a ferrite scope.

In the Publication JP-A-61-28859, a change in the quantity of ferrite is measured using a ferrite scope, so that it is impossible to measure a change in the magnetic characteristic due to the deposition of $\alpha'$ and G phases produced by the spinodal decomposition of the initial ferrite phase.

Japanese Patent Publication JP-A-62-277704 is concerned with superconductors of $Nb_3Sn$ superconducting intermetallic compound, and discloses a method of manufacturing a superconducting sheet coil, comprising the steps of superimposing a substrate containing at least one of two or more metal elements constituting a superconducting intermetallic compound and a metal plate containing the remaining metal element, inserting therebetween an additive member containing a third element, for example, of Ti or Ta, to improve the critical current density in the high magnetic field, and forming a circuit using a heating beam such as a laser beam or an electron beam. According to this method, the superconducting circuit can be produced by adding the third element without alloying the substrate with the metal plate, so that superconducting coils can be manufactured which exhibit an excellent critical current characteristic in a high magnetic field. However, this technique does not involve a method of forming a coil of a recent oxide high-temperature superconducting material nor does it involve a method of manufacturing a superconducting print coil optimal for a low magnetic field.

Another prior art system is disclosed in Japanese Patent Publication JP-A-62-140403. According to this Publication, leads of a superconducting coil used in a deflection electromagnet for an accelerator, etc., are crossed, a plurality of closed curved surfaces are provided in which reverse currents flow, and thus a uniform magnetic field is generated in the vicinity of the central axis of the superconducting coil without deteriorating the critical current characteristic of the elemental superconductors. The above conventional techniques are effective for use in a high magnetic field for accelerators, but the detection of a small magnetic field, for example, by a superconducting quantum interference element (hereinafter referred to also as a "SQUID") is influenced more adversely by external and/or internal noise than the uneven magnetic field generated by the coil parts.

SUMMARY OF THE INVENTION

It is an object of the present invention to provide an apparatus and a method for detecting, with high accuracy and in a non-destructive manner under noisy environments, the degree of deterioration (embrittlement) of an actual plant component which is made of metal material and used in a high-temperature environment.

It is another object of the present invention to improve the sensitivity and the resolution of a superconducting quantum interference element fluxmeter including a flux transmitting circuit (flux transformer).

A fluxmeter of the present invention comprises application means for applying a magnetic field to an object which may be an element of a plant or the like, a transmitting circuit opposingly arranged with the object for detecting a magnetic flux generated at the object by the application means and transmitting a signal indicative of the detected magnetic flux, a superconducting quantum interference element for measuring magnetic characteristics of the object from the signal indicative of the magnetic flux transmitted from the transmitting circuit by magnetic coupling, storage means for storing data of at least the magnetic characteristics of the object in a virgin unused state or of a material in a virgin unused state constituting the object, and determination means for determining the degree of deterioration of the object by comparing the magnetic characteristics of the object being used and the data of the magnetic characteristics of the object or of the material in a virgin state.

The transmitting circuit comprises a pickup coil opposingly arranged with the object for detecting the magnetic flux generated at the object by the application means as a result of applying the magnetic field to the object, a core provided with the pickup coil having a portion which is disposed closer to the object than the pickup coil for guiding the magnetic flux generated at the object to increase the intensity of the signal indicative of the magnetic flux detected by the pickup coil, and a second coil connected to the pickup coil through a plurality of leads for transmitting the signal indicative of the magnetic flux detected by the pickup coil to the superconducting quantum interference element. As magnetic characteristics detected in the superconducting quantum interference element, at least one magnetic characteristic may be selected from a group comprising a residual flux density, a coercive force, a magnetic hysteresis loop area and a magnetic hysteresis figure, for example. Further, a coil made of a superconducting material may be used for the application means for applying the magnetic field to the object so as to magnetize the object efficiently.

Firstly, a principle of the present invention for detecting the deterioration of the object is explained hereinafter.

According to the present invention which attains the above objects magnetization characteristics of a metal material changing as a result of deterioration due to aging of the metal material are measured to decide the degree of degradation of the metal material. The configuration of a magnetic hysteresis, which is representative of the magnetization characteristics of an object made of metal material, shows a clear correspondence with the degree of degradation of the metal material. Thus, by detecting a change in this magnetic characteristic, the degree of degradation of the metal material of the object can be estimated. Further, by means of statistical data processing such as a regression analysis, the degree of degradation of the metal material can be estimated with a high rate of correlation.

Namely, in case that a metal material is used for a long period of time in an environment of high temperature, a change generally occurs in its internal structure, resulting in decreased mechanical strength. Especially, in the case of ferritic stainless steel, its mechanical strength decreases markedly with an increase in the period of aging heat treatment at a high temperature.

The inventors conducted research and studies on the tendency toward embrittlement of a metal material such as ferritic stainless steel due to heating at high temperatures. As a result of the research and studies, the inventors found that, with the progress of aging at high temperatures, the electromagnetic characteristics such as the electrical resistivity $\gamma$ and permeability $\mu$ of the metal material were subjected to a change. Thus, the mechanical properties such as the hardness and the metallographic structure of the metal material were also subjected to a change. Particularly, the inventors found that the tendency toward brittleness of the metal material shows a clear correspondence with a change in the magnetization characteristic of the metal material. The inventors measured a magnetic hysteresis of the metal material in an unused virgin state and that of the metal material in a state treated at high temperature. As a result of the above measurements, the inventors found that the area of the magnetic hysteresis loop (the magnetic hysteresis loss) and the residual magnetic flux density were subjected to a change which was dependent on the degree of brittleness of the metal material. Thus, when such a phenomenon is utilized, the progress of the tendency toward brittleness of a metal material, such as, a ferritic stainless steel, can be detected with high accuracy.

According to the present invention, the degree of brittleness of a metal material used at high temperatures can be detected quickly in a non-destructive way. Therefore, a rupture failure of such a metal material can be prevented before it occurs, and the safety of a plant member made of such a metal material can be improved.

In the transmitting circuit (flux transformer) of the present invention, the pickup coil includes a print coil with a core of a soft magnetic material. The print coil may be either a film-like print coil or a thin-plate print coil. The print coil may be a laminate of two or more sub-print coils. The fluxmeter can also function as a flux gradient meter by changing the directions in which the two print coils are wound. A thin film-like print coil may be manufactured using sputtering, laser sputtering, MBE, MOCVD or spray pyrolysis. A thin film plate print coil may be manufactured fusing a doctor blade.

In the following description, the print coil is discussed as a thin film-like or thin plate-like coil.

A fluxmeter according to the present invention comprises a flux transmitting circuit (flux transformer), including a print coil, disposed so as to face an object to be measured, a superconducting quantum interference element provided within the reach of magnetic flux generated by the flux transmitting circuit. Preferably, the coil has a soft magnetic material core. In this case, the pickup coil is not necessarily required to be a print coil. Preferably, a member (interposition) is inserted between the coil and the object to be measured to define the distance therebetween.

The relationship between the coil and the core has the following aspects:

(1) The soft magnetic core is provided on the opposite side of the print coil from the object to be measured;

(2) The core of a soft magnetic material is disposed between superconducting ribbons of the print coil with the print coil and the core being accommodated in the same plane;

(3) A core is provided which includes an integral unit of the cores mentioned in the items (1) and (2);

(4) The core between the superconducting ribbons of the print coil extends to contact the object to be measured; and (5) Two or more print coils are superimposed.

There are two magnetic shielding methods which can be applied to the fluxmeter. One method covers the whole fluxmeter, except for the print coil which receives magnetic flux, with a magnetic shielding plate. The other method covers, with a magnetic shielding tube, the leads for the magnetic transmitting circuit or flux transformer and covers, with a magnetic shielding plate, the SQUID in the circuit or transformer and the coil for transmitting magnetic flux to the SQUID.

Preferably, the magnetic shielding plate and tube are made of a high permeability material or $\mu$-metal.

In the flux gradient meter according to the present invention, a second print coil opposite in winding direction to the probe coil or pickup coil is provided on the opposite side of the pickup coil from the object to be measured.

Preferably, the pickup coil (probe coil) is a print coil.

A method of manufacturing a print coil is illustrated as follows:

(1) In one method, a mask is placed on a substrate, the mask being beforehand manufactured so as to match the shape of a print coil, and a superconductor target disposed before the mask is sputtered, so that a superconducting thin film coil structure is formed on the substrate.

(2) In another method, a print coil is manufactured using electron beam deposition, laser sputtering deposition, MBE deposition, MOCVD, spray pyrolysis deposition, or a combination of these processes, or a combination of sputtering and one of these processes.

(3) A mixture of superconducting materials is processed by cold working into a line-like material, which is then changed into a coil. The coil is then further changed into a print coil using a doctor blade process and finally sintered.

(4) A mixture of superconducting materials is changed into a plate-like material using a doctor blade process. The plate-like material is then changed into a printed coil using a direct working process and sintered.

(5) A negative image of a print coil is formed on the substrate surface. A thin film is formed on the entire surface of the substrate. The material forming the negative image and the superconducting thin film formed on the material are removed so as to form a negative pattern using a solvent to form a superconducting thin film coil comprising the remainder of the material and film on the substrate.

(6) A positive pattern of a print coil is formed on a superconducting thin film on a substrate surface. The negative pattern is etched away, and a resist forming the remaining positive pattern surface is removed using a solvent or washed in a dry etching process.

(7) A superconducting thin film on a substrate is sputtered with a focused ion beam or implanted with ions and scanned with the ion beam.

(8) A thin film on a substrate is irradiated, heated and scanned with a laser beam, and a negative pattern is formed at a temperature at which a non-superconducting phase is formed. A positive pattern is formed at a temperature at which a superconducting phase is formed.

(9) Superconducting material paste is screen printed on a substrate to form a coil pattern.

(10) Silk screening or a photosensitive resin is used to form the negative image or the coil pattern.

(11) The resulting intermediate is then heated in oxygen or in the atmosphere.

The core used in the present invention is made of a soft magnetic material. The method of manufacturing this core removes any point defects, lattice defects and uneven internal stress due to the separation of impurities. Further, this method easily adjusts magnetization direction by cooling, rolling and recrystallizing the core material in a magnetic field.

The present invention provides a deterioration sensing method in which a magnetic field is applied across an object to be measured, a change in the magnetic characteristic inherent to the object is monitored, and the degree of deterioration of the object is recognized from the change in the magnetic characteristic. The change in the magnetic characteristic is measured using the fluxmeter according to the present invention.

A print coil of a superconducting ribbon is used as a sensing coil in the magnetic transmitting circuit of the superconducting quantum interference element to thereby generally reduce the self-inductance of the pickup coil. The transmissibility $\epsilon$ (sensitivity) of the flux transmitting circuit is increased by the reduction of the self-inductance, and as a result the signal resolution of the fluxmeter is improved. By provision of the soft magnetic core in the print coil, the leakage of magnetic flux passing through the superconducting loop of the print coil is suppressed because the magnetic flux is conducted through the core. Further, the noise produced by an external magnetic field is reduced and thus the sensitivity of the magnetic sensor is greatly improved. A change in the magnetomotive force due to $\alpha'$ and G phase deposited in the ferrite phase of ferrite stainless steel used is a high-temperature environment is measured with accuracy by a fluxmeter according to the present invention because the pickup coil is provided in the vicinity of the sample to be measured.

BRIEF DESCRIPTION OF THE DRAWINGS

FIGS. 2–4 each show the shape of a print coil used in the present invention.

FIG. 7 illustrates the magnetic shielding, against external magnetic noise, for the fluxmeter according to the present invention.

FIG. 14 illustrates a method of manufacturing a thin film print coil of the fluxmeter according to the present invention.

FIG. 20 is a cross section view of a fluxmeter having a print coil positioning element as one embodiment of the present invention.

FIG. 21 is a cross section view of a fluxmeter having a print coil core as one embodiment of the present invention.

FIG. 27 illustrates the application of the inventive fluxmeter to an atomic power vessel.

FIG. 28 illustrates one embodiment of a process of manufacturing an intersection of the print coil of the fluxmeter according to the present invention.

FIG. 31 illustrates one embodiment of a method of manufacturing the inventive fluxmeter in which a Y—Ba—Cu—O system superconducting print coil is applied.

FIG. 33 shows structures of an exciting system and a magnetization sensor system shown in FIG. 32.

FIG. 34 shows a structure of a magnetization control unit shown in FIG. 33.

FIG. 35 shows one form of procedures for measurement by the general system shown in FIGS. 32-34.

FIG. 39 is a graph showing the relation between the magnetizing force and the magnetic hysteresis loop of the metal material in case the magnetic flux density is fixed.

DESCRIPTION OF THE PREFERRED EMBODIMENTS

Embodiments of the present invention will now be described with reference to the drawings.

GENERAL SYSTEM ARRANGEMENT

Figure 32:
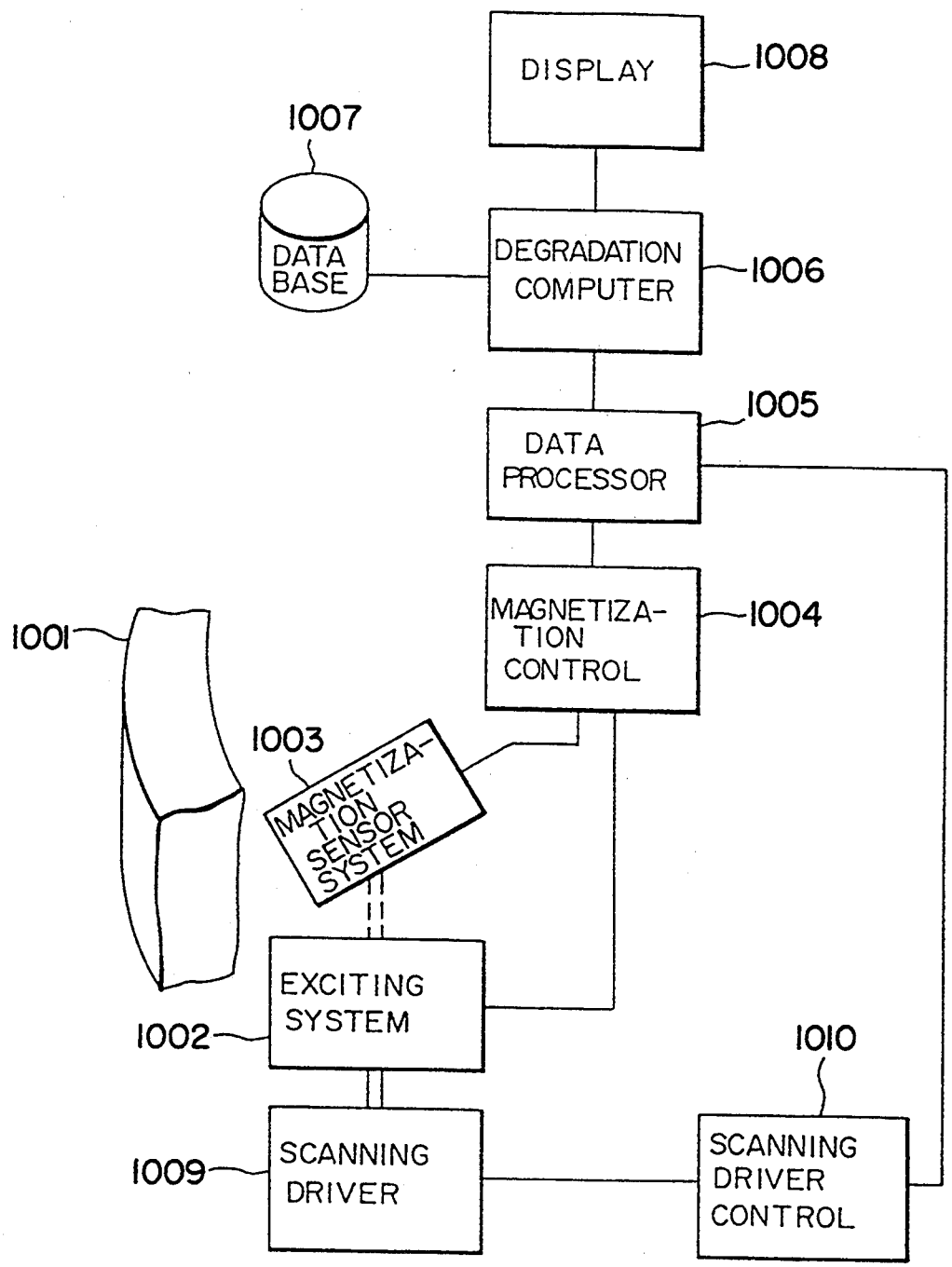
FIG. 32 shows one form of a general system arrangement using the apparatus of the present invention.

FIG. 32 shows one form of a general system arrangement employed for putting into practical use the apparatus of the present invention for detecting deterioration of a metal material.

Referring to FIG. 32 an object 1001 to be measured is a member such as a part of equipment or a part of a piping system of a plant such as a nuclear power plant. An exciting system 1002 magnetizes the object 1001, and a magnetic sensor system 1003 detects the magnetization. The apparatus further includes a magnetization control unit 1004, a data processing unit 1005, a degradation computing unit 1006, a data base 1007 and a display unit 1008. A scanning driver 1009 drives the exciting system 1002 and magnetization sensor system 1003 for scanning movement thereof under control of a scanning driver controller 1010.

The exciting system 1002 and the magnetization sensor system 1003 are disposed opposite to the surface of the measuring object 1001. The scanning driver 1009 for driving the scanning movement of the exciting system 1002 and magnetization sensor system 1003 is electrically connected to the scanning driver controller 1010 to be controlled by the data processing unit 1005.

The exciting system 1002 and the magnetization sensor system 1003 are electrically connected to the magnetization control unit 1004 to magnetize the measuring object 1001 and detect the magnetization under control of the magnetization control unit 1004. The data of magnetization and the data of the detected magnetization are supplied to the magnetization control unit 1004 which sets the optimum conditions for the magnetization. The data processing unit 1005 processes the acquired data for each of the individual degradation parameters. The data processed in the data processing unit 1005 for each of the individual degradation parameters are compared in the degradation computing unit 1006 with corresponding data previously computed and stored as part of the data base 1007, and, after necessary computation in the degradation computing unit 1006, the degree of degradation of the object 1001 is decided. The result of the decision is displayed on the display unit 1008.

EXCITING SYSTEM AND MAGNETIZATION SENSOR SYSTEM

FIG. 33 shows in detail the structure of the exciting system 1002 and magnetization sensor system 1003. Referring to FIG. 33, the exciting system 1002 includes an oscillator 1021 of waveform control type for controlling the waveform of a magnetizing current used for magnetization, an amplifier 1022 for amplifying the oscillation output signal of the oscillator 1021 and an exciting coil 1023 for magnetizing the object 1001. From the amplifier 1022, a signal indicative of the magnetizing force of the exciting coil 1023 is generated. This signal is applied to the magnetization control unit 1004. The symbol i designates the exciting current. A magnetic flux B flowing out from the exciting coil 1023 to flow into the object 1001 is sensed by a magnetization sensor 1031. The output of the magnetization sensor 1031 is applied through a transducer 1032 to the magnetization control unit 1004.

MAGNETIZATION CONTROL UNIT

FIG. 34 shows in detail the structure of the magnetization control unit 1004. Referring to FIG. 34, the magnetization control unit 1004 includes a magnetic hysteresis loop synthesizer 1040, a flux density input interface 1041, a magnetic field intensity input interface 1042, a magnetization characteristic output memory 1043, a reference setting device 1044 and a differential amplification controller 1045.

Data of the magnetic field intensity generated by exciting system 1002 for magnetizing the object 1001 is supplied through the magnetic field intensity input interface 1042 to the magnetic hysteresis loop synthesizer 1040. Data output from the magnetization sensor system 1003, which may be composed of a Hall element or a detection coil and an integrator for sensing the magnetic flux induced by the magnetic field intensity, is supplied through the magnetic flux density input interface 1041 to the magnetic hysteresis loop synthesizer 1040. The data being received is synthesized into a corresponding magnetic hysteresis loop in the magnetic hysteresis loop synthesizer 1040. This synthesized magnetic hysteresis loop is compared with a pre-set reference pattern stored in the reference setting device 1044, and the difference or deviation is amplified by the differential amplification controller 1045. The resultant output of the controller 1045 is fed back to the exciting system 1002 so as to establish the optimum exciting conditions. The data of the optimized magnetic hysteresis loop is supplied to the data processing unit 1005 through the magnetization characteristic output memory 1043.

PROCEDURE FOR MEASUREMENT

FIG. 35 shows one form of the procedure for measurement by the general system shown in FIGS. 32–34 relating to the present invention.

Step 1:
First, the driver 1009 is disposed opposite to the surface of the object 1001 such as part of the associated equipment or pipe in the nuclear reactor and is set at the origin of the measuring system.

Step 2:
The measurement or inspection range is commanded.

Step 3:
The driver 1009 is moved to the starting point of measurement so that the measurement can be started.

Step 4:
The measurement is started, and the measured data at the measurement starting point is acquired.

Step 5:
The acquired data is stored in the magnetization control unit 1004.

Step 6:
After completion of the measurement at the measurement starting point, the driver 1009 is moved to the next measuring position.

Step 7:
Decision is made as to whether or not the driver 1009 has been moved to the final position of measurement.
When the result of decision is "No" the step 7 is followed by the step 4 again; when the result of decision is "Yes" step 7 is followed by a step 8.

Step 8:
All the measured data are transferred from the magnetization control unit 1004 to the data processing unit 1005, and the measured data processed in the data processing unit 1005 are transferred to the computing unit 1006.

Step 9:
The measured data are processed according to a method of statistical data processing, and the data stored in the data base is based to decide the degree of aging degradation. The result of decision is supplied to an external recorder and displayed on the display unit 1008.

DATA PROCESSING

The five methods for the statistical data processing executed in the step 9 of FIG. 35 will now be explained with reference to FIGS. 36–41, for example.

Figure 36:
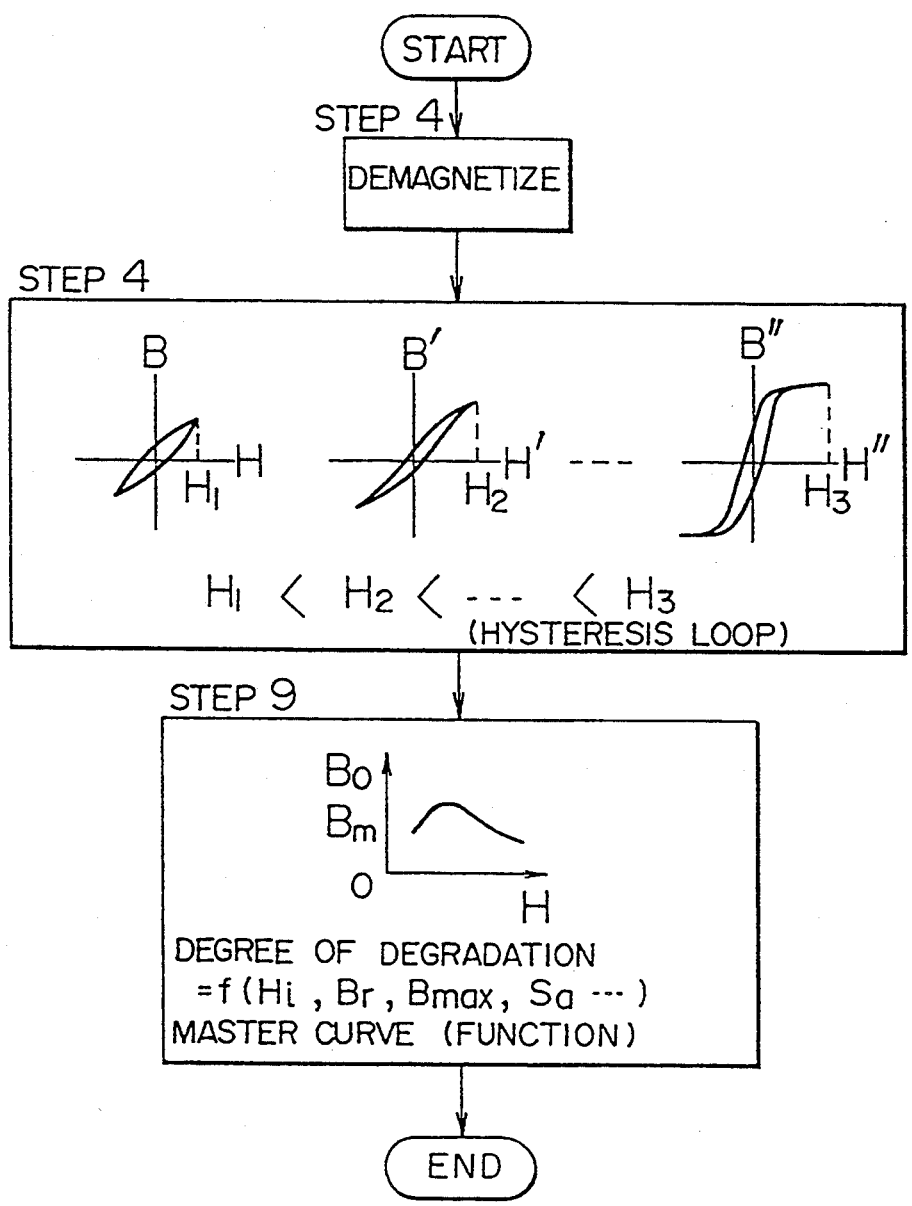
FIG. 36 is a flow chart showing one form of data processing in the procedures shown in FIG. 35.

Firstly, in the step 4 of measurement to acquire data in FIG. 35, it is preferable to demagnetize the object 1001 and detect magnetic hysteresis loops at various levels $H_1, H_2, ---, H_3$ $(H_1 < H_2 --- < H_3)$ of the magnetic field intensity to acquire necessary data as shown in FIG. 36. Then, in the step 9 of data processing, the degree of degradation of the object 1001 is decided on the basis of a previously determined master curve or a previously computed evaluation function as shown in FIG. 36.

Thus, it is preferable that magnetic hysteresis loops of the specific material of the object 1001 are detected by continuously or discretely changing the magnetic field intensity, and the data of the normalized magnetic hysteresis loop area and the data of the normalized magnetic flux density shown are used to prepare a calibration curve. When such a calibration curve is prepared for each of many kinds of stainless steels to provide a data base, and measured data is compared with corresponding data of the data base, the degree of degradation of the object 1001 can be estimated without requiring initial data of the measuring object.

SECOND METHOD OF DECISION

A second form of the method of decision comprises magnetizing a degraded metal material by a predetermined magnetic field intensity and estimating the degree of degradation on the basis of the value detected at that time.

Figure 37:
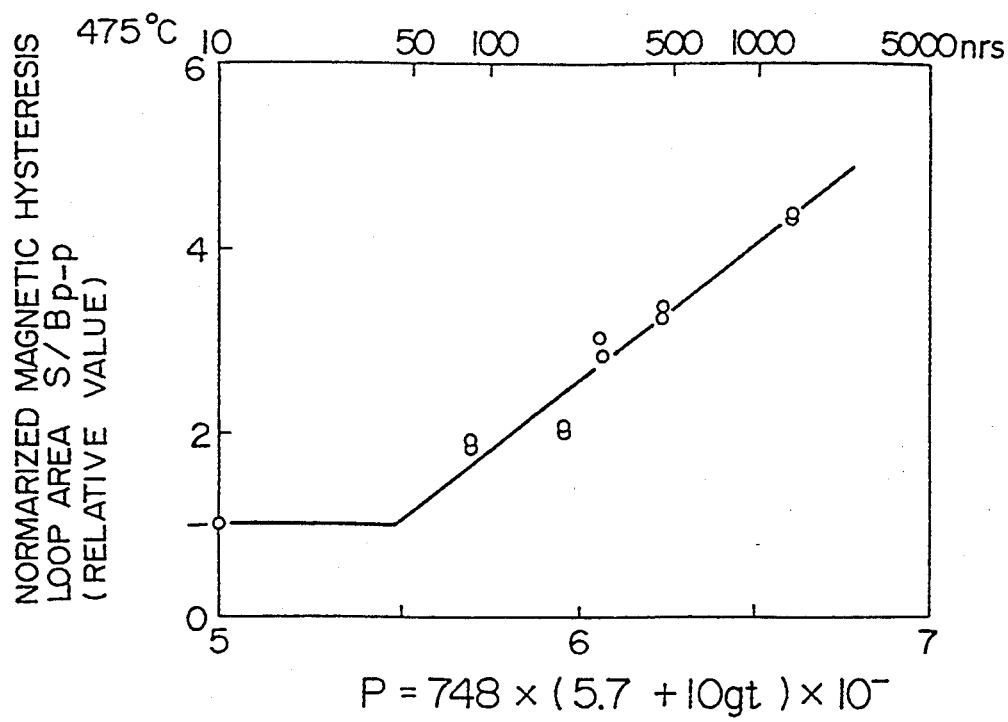
FIG. 37 is a graph showing the relation between the normalized magnetic hysteresis loop area and a degradation parameter of a metal material.

The magnetic hysteresis loop area ratio and the residual magnetic flux density change depending on the magnitude of the magnetic flux intensity, and a clear difference appears between a degraded metal material and an as-received virgin metal material when the magnetic field intensity exceeds a certain limit. Therefore, the magnetic field intensity is set at a value suitable for detection of degradation of a metal material, and the magnetic hysteresis loop of the metal material is measured. FIG. 37 is obtained when the parameters such as the magnetic hysteresis loop area, residual magnetic flux density and maximum magnetic flux density of the metal material are plotted relative to a degradation parameter indicative of the degree of degradation. (This degradation parameter is, for example, the value P in the Lalson-Miller's rule.)

Figure 38:
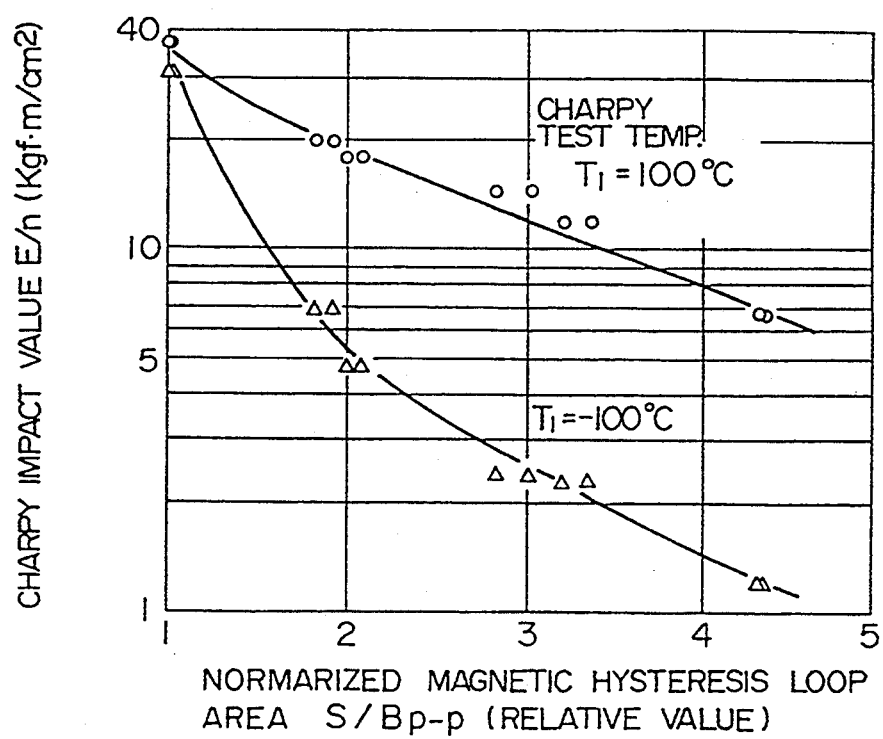
FIG. 38 is a graph showing the relation between the normalized magnetic hysteresis loop area and the Charpy impact value of the metal material.

That is, on the basis of the measured data of the magnetic hysteresis loop area, residual magnetic flux density and maximum magnetic flux density of the metal material, the value of the degradation parameter can be determined. The value P is determined so that the degree of degradation of the metal material can be estimated. Therefore, the degree of degradation of the metal material can be estimated when the data shown in FIG. 37 is used to provide a data base. For example, the metal material may be previously subjected to a Chalky impact test, and the Charpy impact energy or fracture toughness value of the metal material may be used as the degradation parameter of the metal material. When such data shown in FIG. 38 are used to provide part of the data base, the breaking or fracture strength of the metal material can also be estimated.

THIRD METHOD OF DECISION

In the second method of decision described above, the magnetic hysteresis loop of a metal material is measured while setting the magnetic field intensity at a predetermined value. According to a third method, the magnetic hysteresis loop of a metal material is measured while setting the magnetic flux density at a predetermined value as shown in FIG. 39. In the third method, the magnetic flux density used for exciting the metal material is fixed so as to control the magnetic field intensity with high accuracy during measurement of the magnetic hysteresis loop. Therefore, the reproducibility and accuracy of the measured data can be easily improved.

FOURTH METHOD OF DECISION

According to a fourth method of decision, the degree of degradation of a metal material is estimated on the basis of the pattern of the magnetic hysteresis loop of the metal material.

Figure 40:
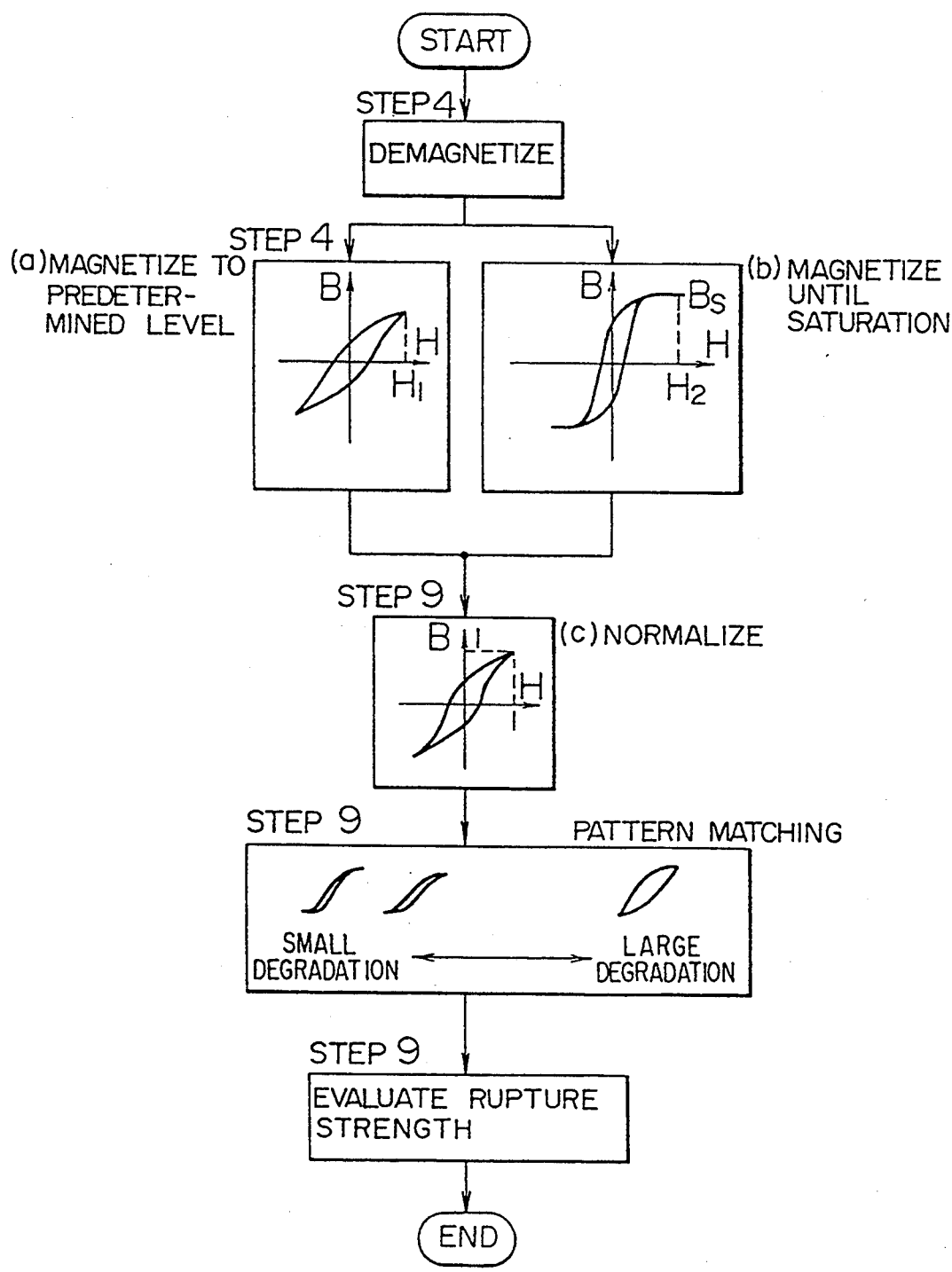
FIG. 40 is a flow chart showing the steps for estimating the degree of degradation of a metal material on the basis of the pattern of the magnetic hysteresis loop.

The pattern of the magnetic hysteresis loop of a metal material shows a correspondence with the degree of degradation of the metal material. FIG. 40 is a flow chart showing how the degree of degradation of a metal material is estimated on the basis of the pattern of the magnetic hysteresis loop.

In the step 4 of measurement and data acquisition in the flow chart of FIG. 40, an object is demagnetized, and necessary data is acquired from a magnetic hysteresis loop produced by magnetizing the object to a state of predetermined magnetization or by magnetizing the object to a state of magnetic saturation. In step 9 of acquired data processing, the magnetic hysteresis loop is normalized and the pattern of the normalized magnetic hysteresis loop is used for pattern matching with previously determined reference hysteresis loop patterns stored in a data base. As a result of the pattern matching, the magnetic hysteresis loop most analogous to the pattern of the measured magnetic hysteresis loop is selected from the data base and the degree of degradation or fracture strength of the object is estimated on the basis of the degree of degradation of the selected magnetic hysteresis loop.

FIFTH METHOD OF DECISION

Figures 41A, 41B, 41C:
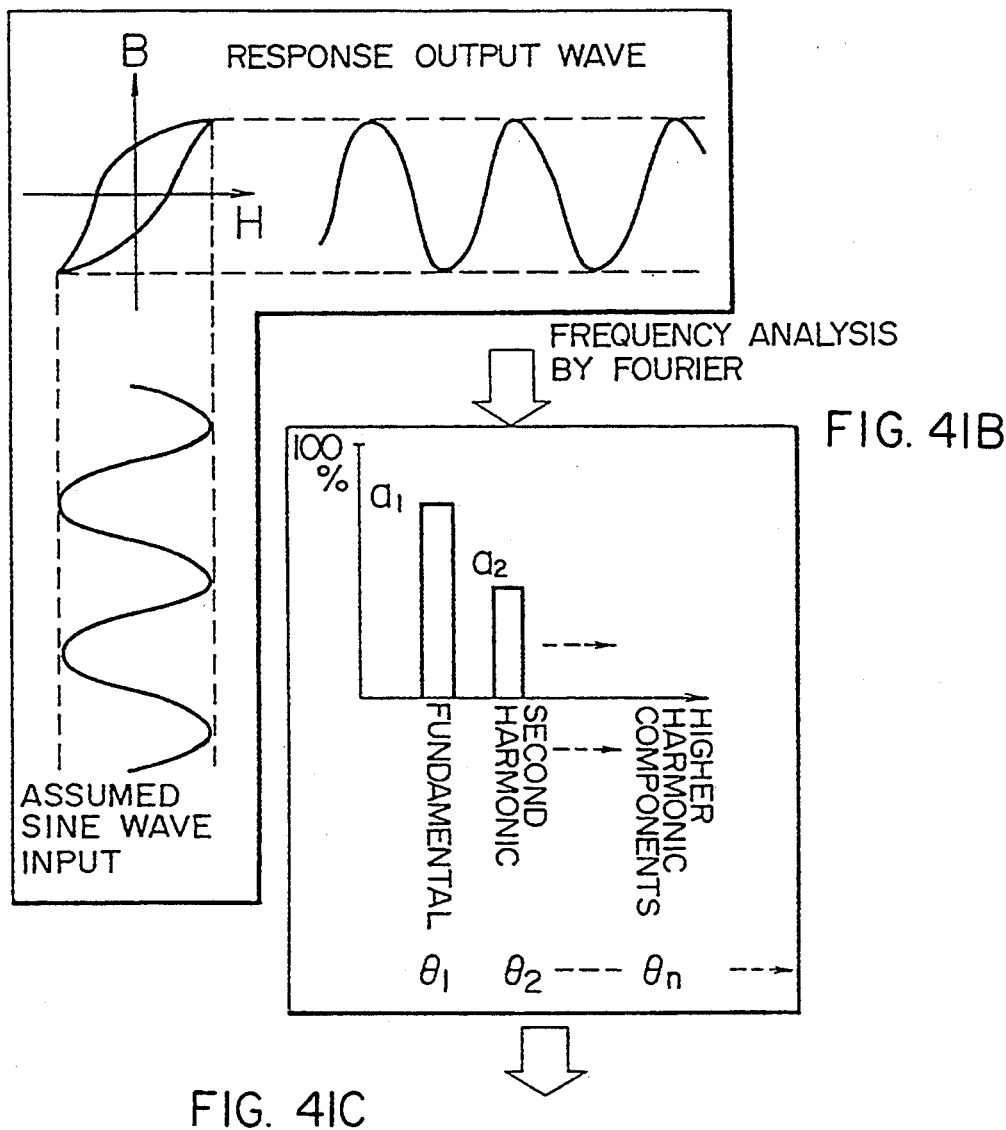
FIG. 41 is also a flow chart showing the steps for deciding the degree of degradation of a metal material by means of the Fourier transformation of data of the magnetic hysteresis loop of the metal material.

FIG. 41 shows a fifth method of decision. In step 9 of data processing in the flow chart of FIG. 35, the measured magnetic hysteresis loop is used to detect the output waveform of the magnetic flux density when a sine wave input is applied to generate the magnetic field intensity and output waveform distortion of the magnetic flux density is computed by Fourier transformation. Then, on the basis of the magnitude and phase difference of individual higher harmonic components, the degree of degradation of the metal material is detected from the data base which has stored therein data computed according to a technique of statistical data processing such as a regression analysis.

(Structure of a Magnetic Sensor)

Figure 1:
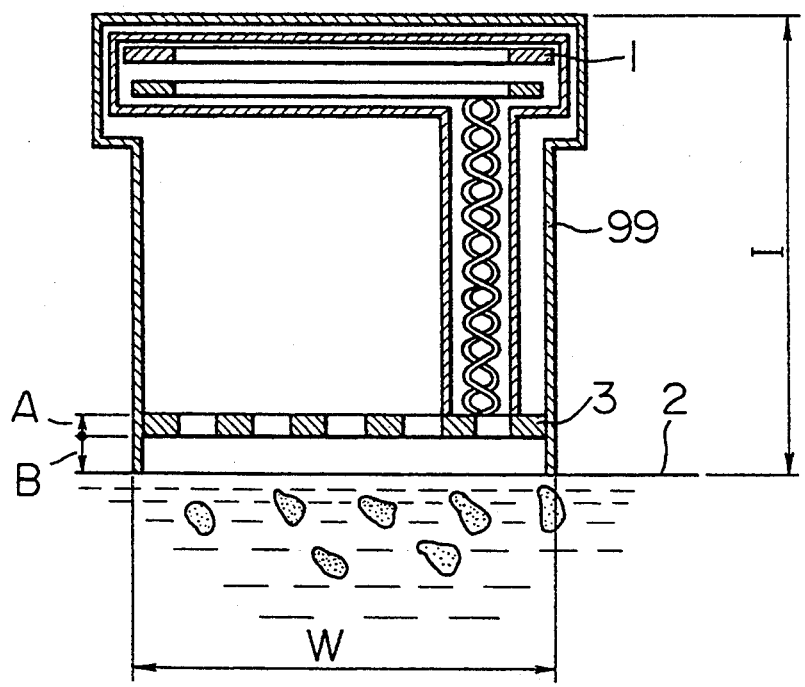
FIG. 1 is a cross section view of a fluxmeter according to the present invention.

FIGS. 1, 20-25 each are a schematic of a fluxmeter (a magnetic sensor) as an embodiment of the present invention. In the embodiment of FIG. 1, a superconducting quantum interference device (SQUID) 1 is provided above in the fluxmeter, and a pickup coil 3 comprising a print coil is provided in the vicinity of a sample 2 to be measured. The SQUID 1 and pickup coil 3 are protected by a shield 99 from external noise. As shown in FIG. 1, the fluxmeter is sized to be about 20-200 mm in diameter W, and about 50-200 mm in height I. The pickup coil 3 is about 50 $\mu$m-3 mm in thickness A, and put either in intimate contact with or closely spaced from the sample 2. In the latter case, the pickup coil 3 is separated from the sample 2 by a distance B of about 100 $\mu$m-5 mm. It may be formed of either a thin film or a thin plate. The pickup coils 3 of FIGS. 1, 20-25 are shown as being formed of a thin plate. In order to define the distance between a pickup coil 4 and a sample 2 in the embodiment of FIG. 20, a member 5 substantially equal to 1 (unity) in relative permeability is inserted between those elements to suppress the absorption loss of flux. The material of the member 5 is preferably an organic insulating material such as polyethylene or Teflon (trade name) or an inorganic insulating material. The print coil can measure a slight change in the magnetic flux in the sample 2 to thereby improve the sensitivity and signal resolution of the magnetic sensor.

The leads 24 couple the pickup coil to the SQUID and are components of the flux transmitting circuit. The leads 24, which are twisted to reduce noise, serve to transfer the detected magnetic field to the SQUID 1.

Figure 22:
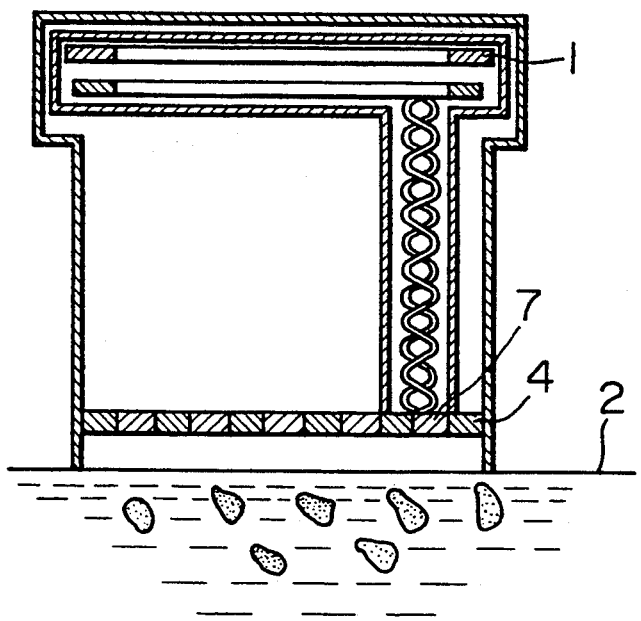
FIG. 22 is a cross section view of a fluxmeter as one embodiment of the present invention in which a print coil and its print coil core are formed on the same plane.
Figure 23:
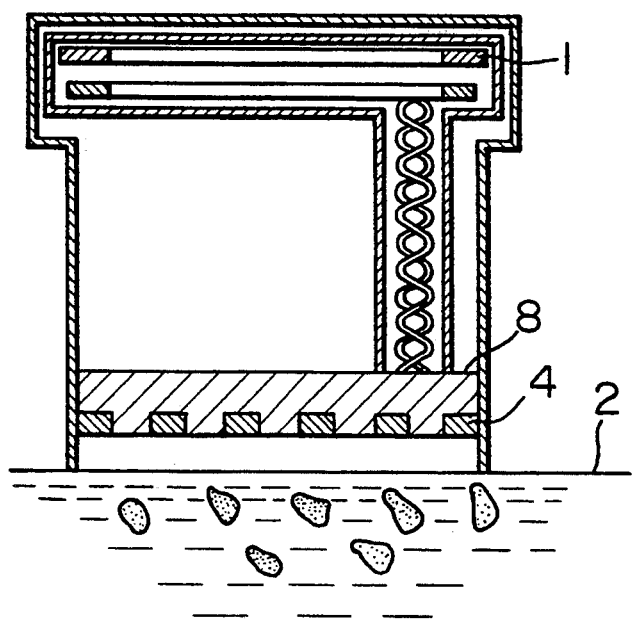
FIG. 23 is a cross section view of a fluxmeter as one embodiment of the present invention in which print coil cores are formed as an integral unit.
Figure 24:
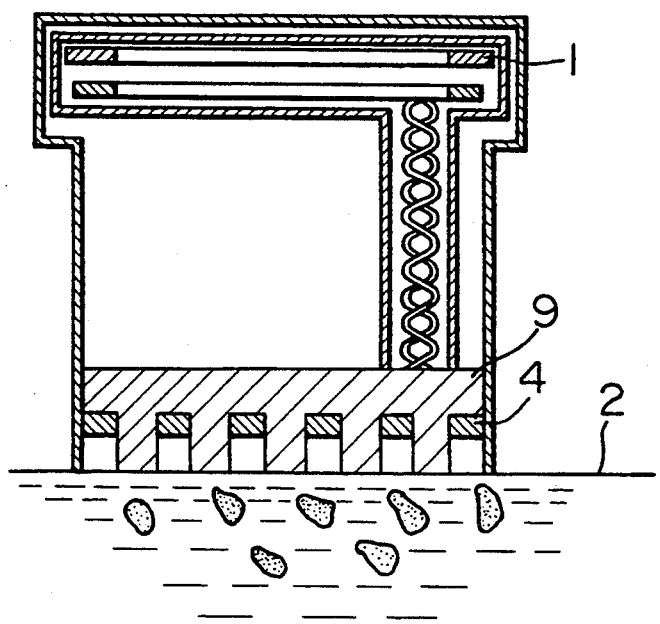
FIG. 24 is a cross section view of a fluxmeter as an embodiment of the present invention in which a print coil core is extended toward a sample to be measured.

In the embodiment of FIG. 21, a print coil core (A) 6 of a soft magnetic material is provided on the opposite side of the print coil 4 from a sample to be measured 2. Sendust and iron-nickel alloy such as Permalloy (trade name) (PC) and high hardness Permalloy (HPC) low in hysteresis loss or a ferrite material resistant to high frequencies is effective for the soft magnetic materials. By the provision of this print coil core (A) 6, the leakage of a flux passing through the print coil 4 is suppressed to increase the intensity of the signal in the magnetic sensor. In the embodiment of FIG. 22, a print coil core (B) 7 is fitted between superconducting ribbons of the print coil 4, and the print coil 4 and the core (B) 7 are provided in the same plane. In the embodiment of the FIG. 23, a print coil core (C) 8 comprising the print coil cores (A) 6 and (B) 7 of FIGS. 21 and 22 as an integral unit was provided. In the embodiment of FIG. 24, the core between the superconducting ribbons of the print coil 4 of FIG. 23 was extended toward a sample to be measured and a print core (D) 9 is provided contacting the sample to be measured 2. By the print coil core (D) 9, the magnetic flux emitted from the sample 2 is directly conducted into the core, so that the leaking flux decreases, noise is cancelled and thus the sensitivity of the magnetic sensor is improved.

Figure 25:
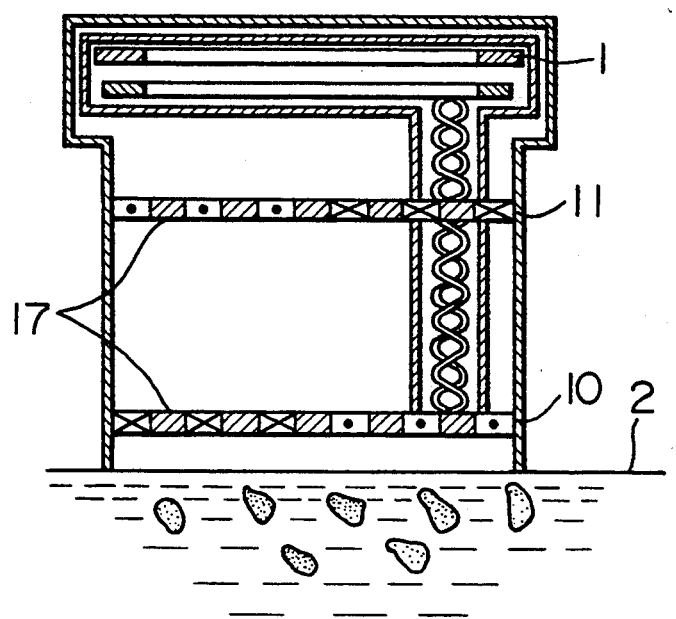
FIG. 25 is a cross section view of a fluxmeter as one embodiment of the present invention and having two pickup coils and capable of measuring a flux gradient.

FIG. 25 schematically illustrates the use of the fluxmeter as a flux gradient meter. The fluxmeter includes a flux transmitting circuit including a series connection of two pickup coils equal in self-inductance, one lower pickup coil 10 being provided in the vicinity of the sample 2 to be measured while the other upper pickup coil 11 being provided in the opposite direction of the lower pickup coil on the opposite side of the pickup coil 10 from the sample. In this case, two uniform magnetic fields cancel each other, so that only the difference between the fluxes picked up by the two pickup coils is delivered as a signal to the SQUID. There are many other conceivable methods of disposing a core. For example, a core 17 may be disposed as shown in FIG. 25. The particular flux gradient meter can sense the distribution of $\alpha'$ and G phases in the direction of depth generated in the ferrite phase and the uniform external magnetic fields are cancelled, so that this fluxmeter is more advantageous in shielding and reducing S/N signals to noise ratio than the aforementioned fluxmeter.

As just described above, the fluxmeter of FIG. 25 includes two pickup coils, so that it can measure the relative value, direction and gradient of the flux while the aforementioned fluxmeter is directed to the measurement of the absolute flux value.

Figure 26:
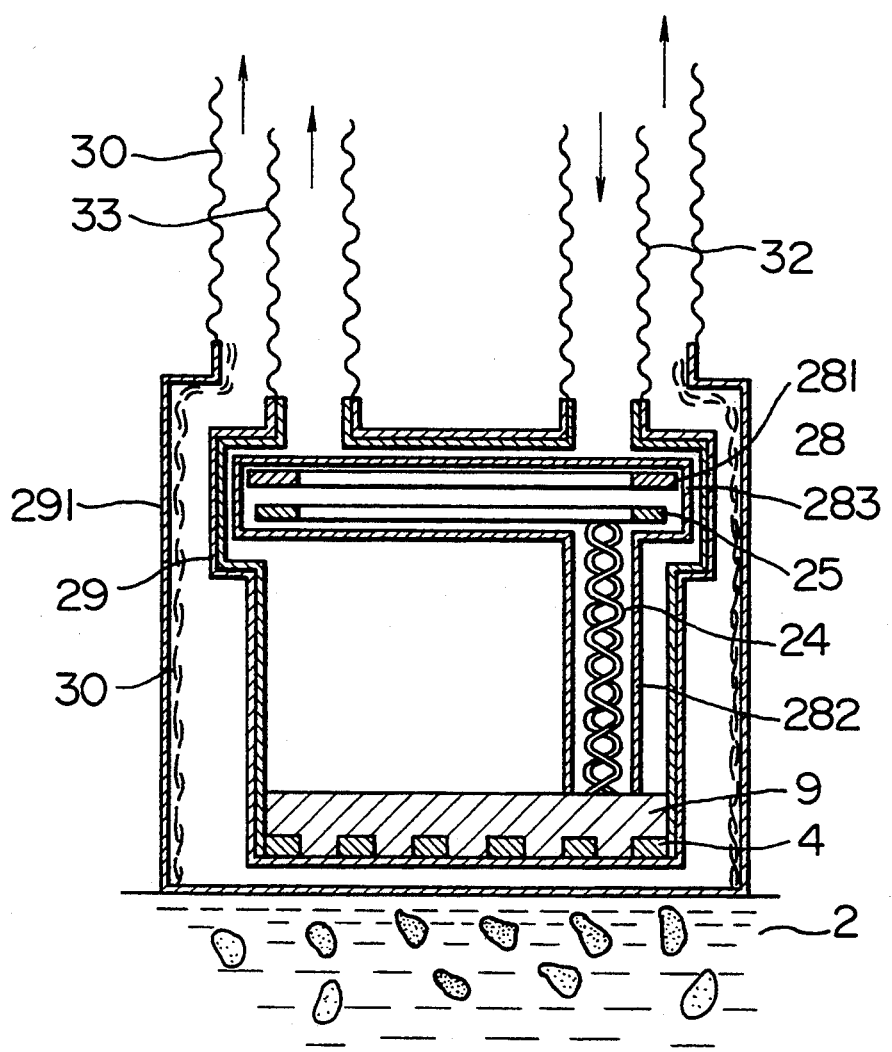
FIG. 26 is a cross section view of a cooling device for a fluxmeter according to the present invention.

FIG. 26 shows an inventive fluxmeter with a cooling system. The magnetic shielding plate 281 of the fluxmeter having a shape shown in FIG. 23 is surrounded by an inner vacuum vessel 290, which is provided within an outer vacuum vessel 291. The outer vessel 291 is evacuated through a flexible tube 300. By this evacuation, the fluxmeter is thermally isolated from the sample to be measured. The inner wall of a reactor pressure vessel which is one of the samples to be measured 2 is immersed in the reactor water at a temperature of about 60° C. in regular inspection. In order to improve the efficiency of thermal isolation between the reactor water and fluxmeter, a multilayered-isolation layer 310 is attached to the inner surface of the outer vacuum vessel. Liquid helium or nitrogen is introduced via a flexible supply tube 320 into the inner vacuum vessel 290 and discharged via a flexible return tube 330. By this cooling medium, the print coil 4, leads 24, coil 25 and rfSQUID 28 are cooled to a temperature at which they operate in a superconducting state. If the print coil 4 is made of a Nb—Ti system and the rfSQUID 28 is made of a Nb superconducting material, liquid helium is introduced while if they are both made of a Y, Bi or Tl system superconducting material, liquid nitrogen is introduced. The structure of the fluxmeter such as the outside vacuum vessel 291 is made of either stainless steel or reinforced plastic.

FIG. 27 is a cross section view of an atomic power vessel to which the inventive fluxmeter is applied. When the long-term embrittlement of the reactor pressure vessel wall 933 is to be detected, the outer vacuum vessel with the inventive fluxmeter is attached to drive shafts 934 and 935, which are connected in a gear box 936. The outer vacuum vessel 291 is moved in the X direction by an X axis motor 938 and also moved in the Y direction by a Y axis motor 937. The gear box 936 is supported by a frame 939, which is fixed at four points on a reactor wall 933 by suckers 940, as shown. The suction between the suckers 940 and reactor wall 933 is performed by discharging the reactor water within the suckers 940 using a vacuum pump 941. The frame 939 is suspended by cables 942 and movable vertically and horizontally by a crane (not shown) disposed above the pressure vessel with an open cap.

Figure 4:
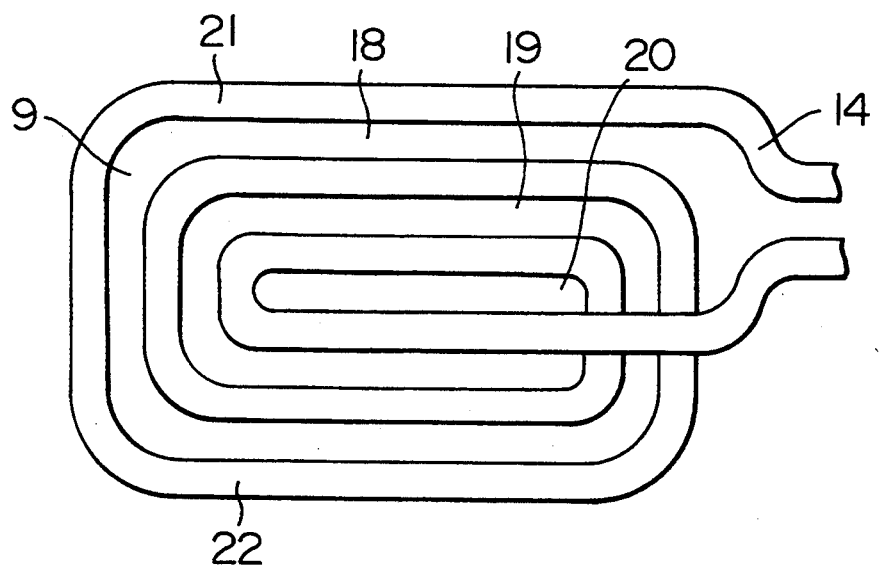

FIGS. 2-4 show the shape of the embodiments of the print coil of FIGS. 1, 20-25. The print coil A 12 of FIG. 2 takes the form of combined juxtaposed superconducting ribbons and can measure magnetic flux passing through grooves 15, and 17 forming a superconducting loop. However, it cannot measure magnetic flux passing through a groove 16, so that a loss is produced in that groove. In the print coils (B) 13 and (C) 14 of FIGS. 3 and 4, respectively, the groove 18 has the self-inductance of a loop comprising superconducting ribbons 21 and 22 and a flux signal intensity corresponding to that inductance while the groove 19 additively has the self-inductance of the inner superconducting ribbon and a flux signal intensity corresponding to that inductance. Thus, as a result the groove 20 provides the maximum flux signal intensity. The print coil (C) 14 has round corners compared to the print coil (B) 13, so that it serves to reduce the resistance to the current. The above print coils are effective for samples of a metal material in which depositions which influence the magnetic flux are locally distributed.

Figure 5:
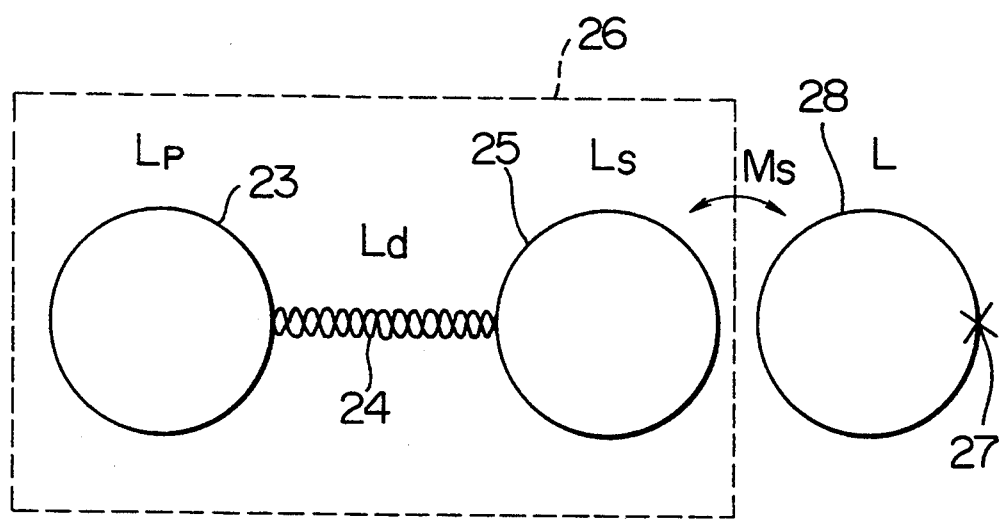
FIG. 5 illustrates the principles of the fluxmeter according to the present invention.
Figure 6:
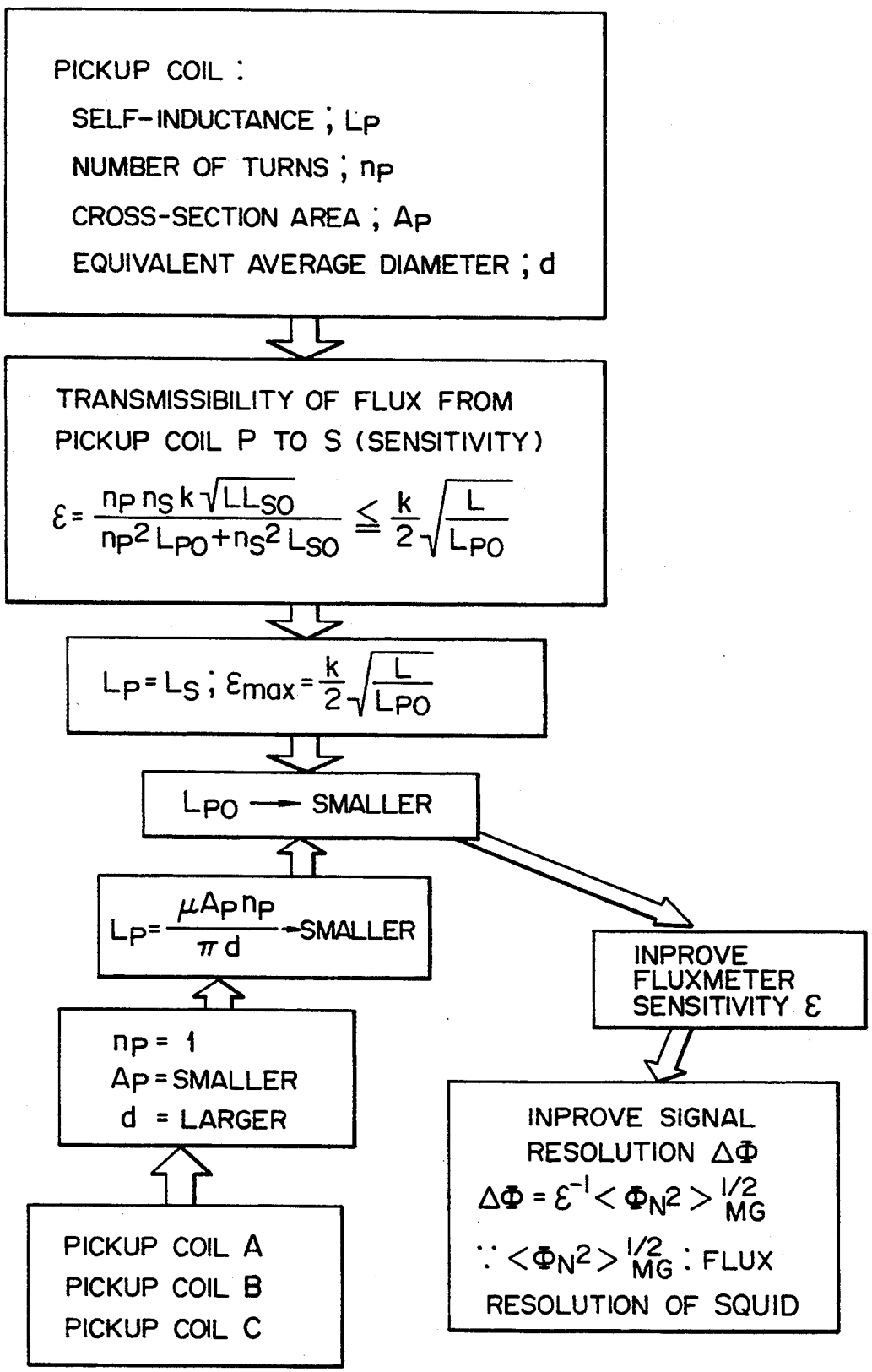
FIG. 6 is a block diagram to explain the improved sensitivity and resolution of the fluxmeter according to the present invention.

The pickup coil P 23 and coil S 25 of FIG. 5 are connected via leads 24 to thereby constitute a closed superconducting circuit 26. The coil S 25 is coupled via a mutual conductance Ms to an rfSQUID 28 having a single Josephson junction 27. The self-inductance Ld of the leads should be reduced as much as possible by twisting the leads sufficiently. If the pickup coils shown in FIGS. 2-4 are used, the sensitivity and signal resolution of the fluxmeter are improved compared to a conventional circular multiwound pickup coil. The reason for this will be described with reference to FIG. 6. The transmissibility $\epsilon$ of the magnetic flux from the pickup coil P 23, indicative of the sensitivity of the fluxmeter, to the coil S 25 is represented by the equation of FIG. 6 where Lp is the self-inductance of the pickup coil P 23, np is the number of turns of the coil P 23, Ap is the cross section area of the coil P 23, d is the average diameter of a single-turn circular coil equivalent to the pickup coil P 23, Ls is the self-inductance of the coil S 25, Ns is the number of turns of the coil S 25, Lpo and Lso are the self-inducatances of one turn of the pickup coil P 23 and coil S 25, respectively. The transmissibility $\epsilon$ is at the maximum when Lp=Ls and the maximum sensitivity is as shown. Therefore, by reducing the self-inductance Lpo of one turn of the sensing coil, the sensitivity $\epsilon$ and signal resolution $\Delta\Phi$ of the fluxmeter are improved. In the pickup coils (A) 12, (B) 13 and (C) 14, np=1, the cross section area Ap is small, and the average diameter d is large compared to the conventional pickup coils, so that Lpo is reduced advantageously.

As shown in FIG. 7, as a measure to counter external noise, the whole fluxmeter except on the side of the print coil which senses the flux from the sample to be measured 2 is covered with a magnetic shield 281 such as $\mu$-metal 281 to reduce the external flux to about $10^{-4}$ G. Leads 24 for the flux transmitting circuit are magnetically shielded by causing the leads to pass through a magnetic shield lead tube 282. The SQUID 28 and the coil S 25 which transmits flux to the SQUID 28 are also shielded with a magnetic shield 283, for example, of PC material, to thereby sufficiently suppress noise due to external flux.

Figure 8A:
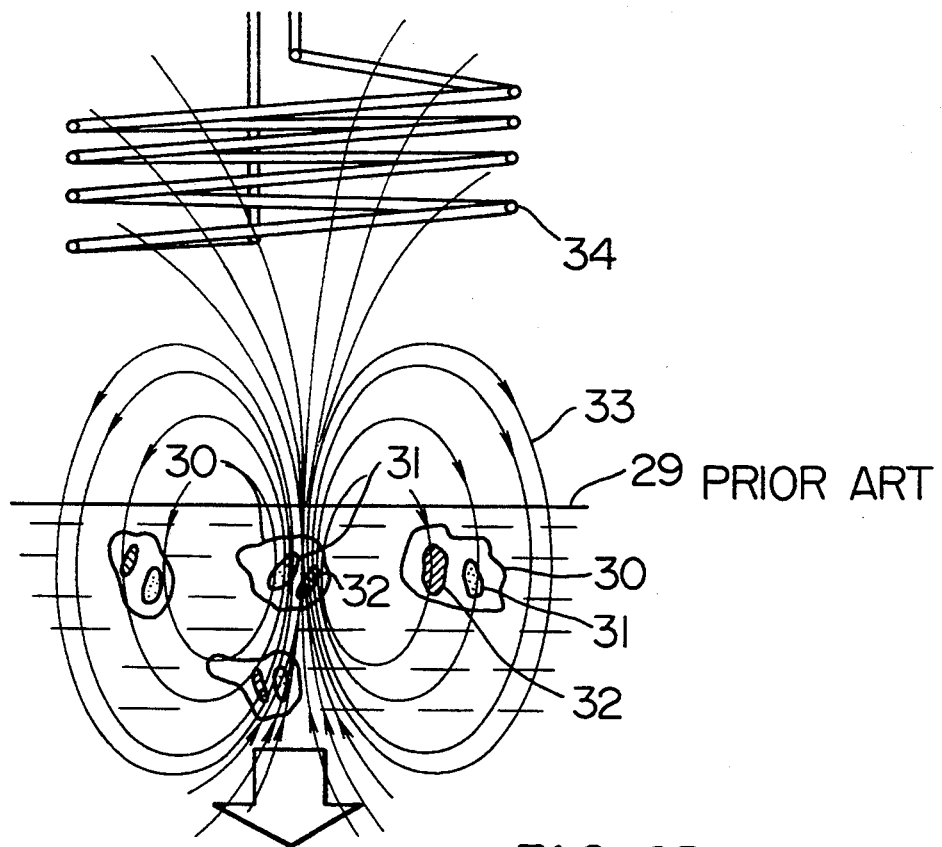
FIG. 8 is schematic cross section views of a conventional fluxmeter and the inventive fluxmeter used to describe the difference in flux measurement between the conventional and inventive fluxmeters.
Figure 8B:
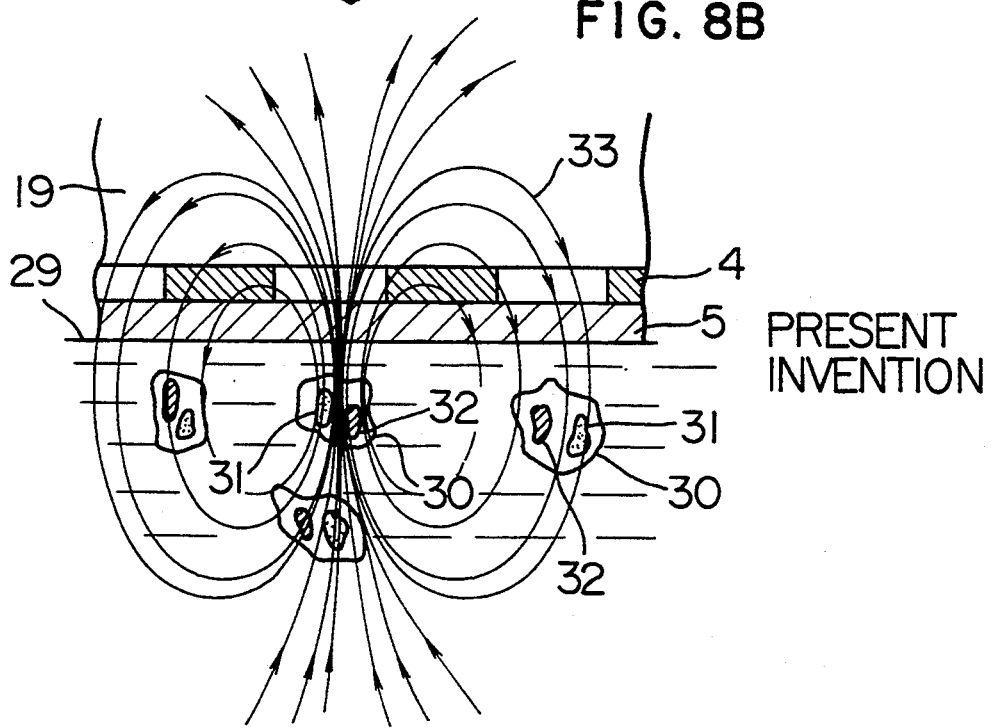

In FIG. 8, samples to be measured in FIGS. 1, 20-25 are ferrite stainless steel 29 used under a high temperature environment such as a chemical plant or an atomic power plant. If the stainless steel 29 is used for a long term under high-temperature conditions, its internal organization changes and its strength is reduced. As shown in FIG. 8, a change in the internal organization is due to the spinodal decomposition of a ferrite phase 30 in the steel and $\alpha'$ and G phases 31 and 32 are deposited in the ferrite phase 30. If the sample is magnetically erased by a magnetic eraser (not shown) and then magnetized by an excitation system (not shown) with an exciting coil (also not shown), the magnetic flux 33 generated by the ferrite phase 30 is as shown in FIG. 8. However, if the conventional pickup coil 34 is used, it is distant from the sample to be measured, so that a high flux density area cannot be measured and the measuring sensitivity of a change in the flux density due to a small deposition is low. If a print coil 4 of the particular embodiment is used, it can access a small deposition, so that changes in the flux density due to $\alpha'$ and G phases 31 and 32 can be measured with high sensitivity. By inserting a thin plate 5 close in relative permeability to 1 (unity) and holding the print coil 4 adjacent the thin plate 5, fluctuations of the distance between the print coil 4 and a sample of ferrite stainless steel are reduced, so that the sensitivity is further improved.

Figure 9:
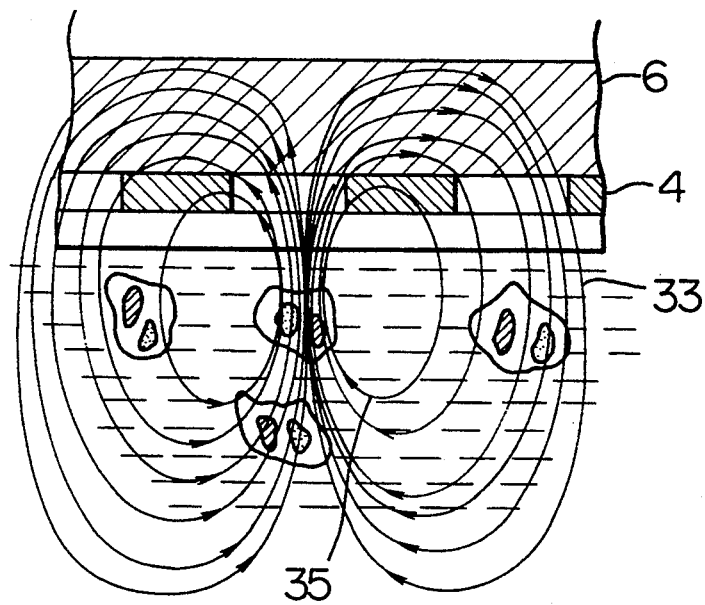
FIG. 9 is a schematic cross section view of the inventive fluxmeter shown in FIG. 21 used to explain the flux measurement of the fluxmeter according to the present invention.
Figure 10:
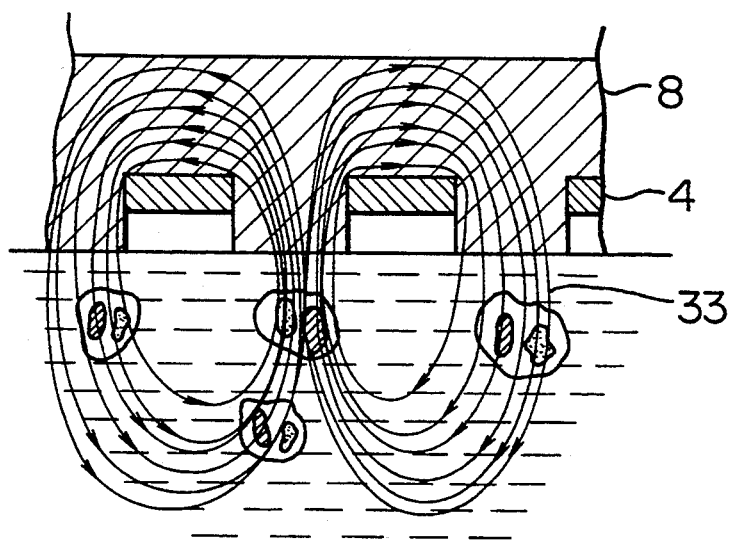
FIG. 10 is a schematic cross section view of the invention fluxmeter shown in FIG. 24 used to explain the flux measurement according to the invention fluxmeter.

FIG. 9 shows the distribution of magnetic flux present when the ferrite stainless steel 29 is measured by the magnetic sensor of FIG. 21. The magnetic flux is induced by the print coil core 6 to thereby reduce the leaking flux compared to the use of only the print coil 4 of FIG. 8. As shown in FIG. 10, if the stainless steel 29 is measured by the magnetic sensor of FIG. 24 the following are achieved: further suppression of the leaking flux, improvement to the sensitivity and reduction of noise. These are achieved because the magnetic flux (2) 35 which cannot reach the print coil in FIG. 9 is induced by the print coil core 8 of a soft magnetic material.

Figure 11:
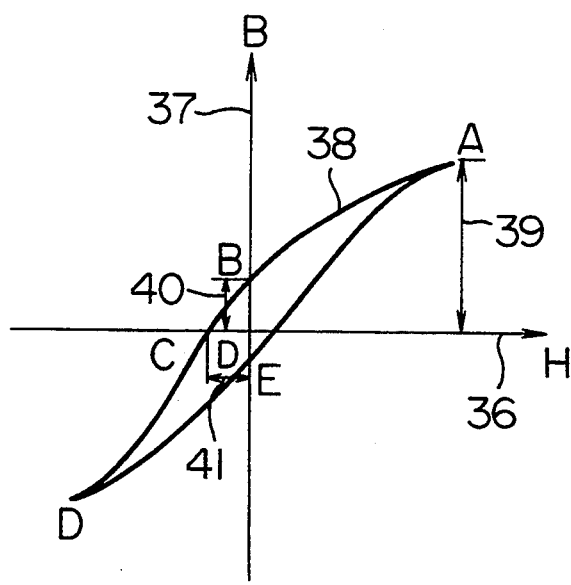
FIG. 11 illustrates the magnetic hysteresis characteristic of ferrite stainless steel when received (before use).
Figure 12:
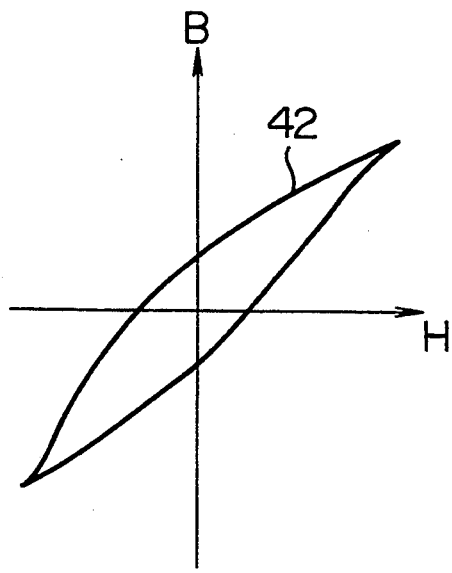
FIG. 12 illustrates the magnetic hysteresis characteristic of deteriorated ferrite stainless steel measured by a conventional fluxmeter.
Figure 13:
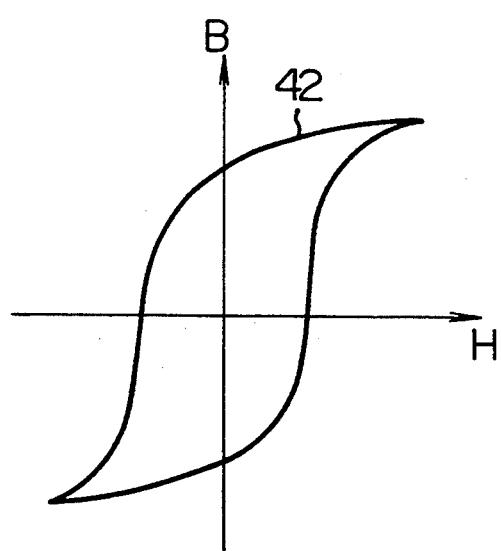
FIG. 13 is a characteristic similar to FIG. 12 and measured by the fluxmeter according to the present invention.

FIG. 11 shows the flux density 37 (B)—magnetomotive force 36 (H) characteristic of the ferrite stainless steel 29 which is a material inserted before it is used for a long term under high-temperature ambient conditions. The magnetization curve due to the magnetomotive force 36 forms a magnetic hysteresis loop 38, so that the maximum flux density 39, the residual flux density 40 and coercive force 41 or hysteresis area 42 can be measured. The maximum flux density 39 depends on the initial quantity of ferrite in the material. If a material, which has deteriorated due to long term use under high-temperature ambient conditions, is measured using the conventional pickup coil 34 and the inventive print coil 4, the measured flux density 37, and magnetomotive force 36 characteristics are shown in FIGS. 12 and 13, respectively. As is obvious from these Figures, the use of the inventive magnetic sensor greatly improves the sensitivity of measurement of the hysteresis area 42 and residual flux density 40.

A method of manufacturing the print coils will be described, using sputtering deposition, electron beam deposition, laser sputtering deposition, MBE deposition, MOCVD and spray pyrolysis deposition.

First, the formation of a print coil using sputtering deposition will be described. In sputtering deposition, a substrate, for example, of MgO, is disposed within a manufacturing container, a mask matching a print coil pattern is placed on the substrate, and a target of a superconducting material such as BiSiCaCuO placed in the manufacturing container is sputtered in a rare gas plasma, for example, of argon, to thereby form a superconducting thin film coil product on the substrate.

The formation of a print coil using electron beam deposition will now be described. In electron beam deposition, a source of metal including superconducting substance is irradiated with an electron beam in high vacuum to thereby evaporate the metal to deposit the flux on the substrate. Higher vacuum, for example, about $10^{-8}$ Torr, is desirable. However, a Nb thin film of a transition temperature Tc=9.8° K can be formed on a quartz substrate at a film forming rate of tens of nanometers/minutes at a substrate temperature of 500° C. or higher even under a vacuum of about $10^{-5}$ Torr, and the transition temperature Tc is higher than the bulk.

FIG. 14 illustrates the formation of a thin film print coil according to the present invention using electron beam deposition. A mask 44 matching a print coil configuration is placed beforehand on a quartz substrate 43 under a vacuum, for example, on the order of $10^{-8}$ Torr. The substrate is rotated while being heated at 600° C. Vacuum evaporated Nb flux 45 is applied to the mask 44 from above using electron beam irradiation to form a thin film print coil 46 in the grooves in the mask 44.

Figure 15:
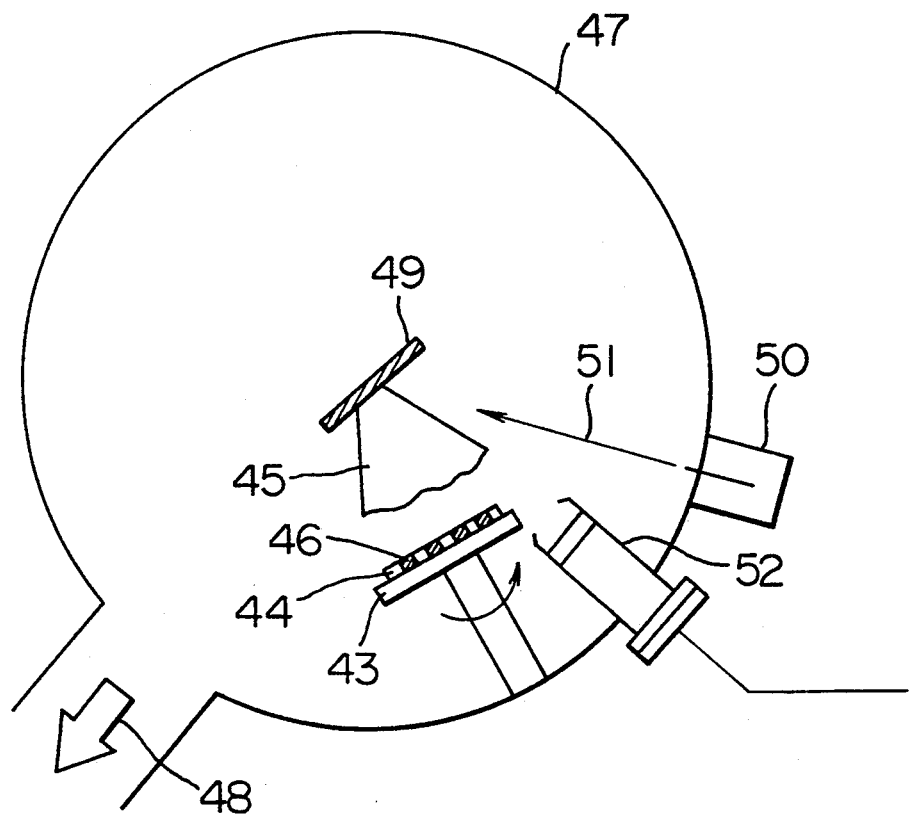
FIG. 15 illustrates the manufacture of a thin film print coil of a fluxmeter according to the present invention using a laser beam deposition process.

Laser beam deposition will now be described. As shown in FIG. 15, a mask 44 is formed, for example, on a MgO substrate 43, with the whole intermediate being introduced into a vacuum container 47, which is then evacuated to a vacuum of $10^{-10}$–$10^{-11}$ Torr. A target of a superconducting material including sintered BiSiCaCuO 49 is provided at the center of the vacuum container 47. The target 45 is irradiated with a laser beam 51 from an excimer laser 50 to generate a flux 45 to thereby grow a thin film print coil 46 on the substrate 43. The state of the flux 45 is monitored by a quadrupole mass spectrometer 52. For example, an ArF excimer laser (its wavelength is 193 nm) as a laser source is used to irradiate an output laser beam of 30 mJ/pulse at 20 Hz for 20 minutes to thereby form a 1 μm superconducting film. In this case, high vacuum is needed but the substrate need not be heated.

The formation of an oxide superconductor print coil using the MBE deposition will be described. A superconducting film is formed by heating a MgO substrate up to 600° C. using, as an evaporation source, for example, of metal Ba, metal Cu or rare earth metal, and a solid oxygen source of $Sb_2O_3$ under a superhigh vacuum on the order of 10-11 Torr.

The formation of a print coil using MOCVD will now be described. In order to form, for example, a YBCO film, organic compound materials $Y(DPM)_{3'}$ $Ba(DPM)_{2'}$ and $Ca(DPM)_2$ are vaporized. The temperatures of the corresponding gas produce from the vaporization is maintained at 130°-160° C., 280°-300° C., and 140°-170° C., respectively, and carried together with Ar carrier gas into a reaction chamber at a flow rate of 200 cm$^3$/minute. At the same time, refined oxygen gas is also fed to the reaction chamber at 200-500 cm$^3$/minute. The substrate temperature should be 600° C. Under these conditions, a YBCO thin film is formed at a growth rate of 0.1-10 μm/hour.

The formation of a print coil using spray pyrolysis will be described. This method includes spraying an aqueous solution containing superconducting substance against a heated substrate in an atmosphere in the atmosphere, and heat treating the resulting intermediate in the atmosphere to thereby form a superconducting film. This method has the following advantages: a superconducting film can be formed on a substrate having a complicated shape, a prepared composition ratio of substances in an aqueous solution becomes the composition ratio of the formed film, the film forming rate is high and film thickening is easy. For example, in order to form a Bi superconductor, respective nitrates corresponding to Bi, Sr, Ca and Cu are mixed at a ratio of 1:1:1:2 to form an aqueous solution. This solution is sprayed in an atmosphere against the substrate, which is heated at 400° C. At this time, water which is a solvent is vaporized instantaneously. Most of the Cu nitrates are changed to oxides in several seconds and Bi nitrates are also changed partially to oxides. Finally, if an 860° C.×10 minute heat treatment is performed in air, the remaining metal changes nitrates to oxides to thereby form a superconducting print coil.

Figure 16:
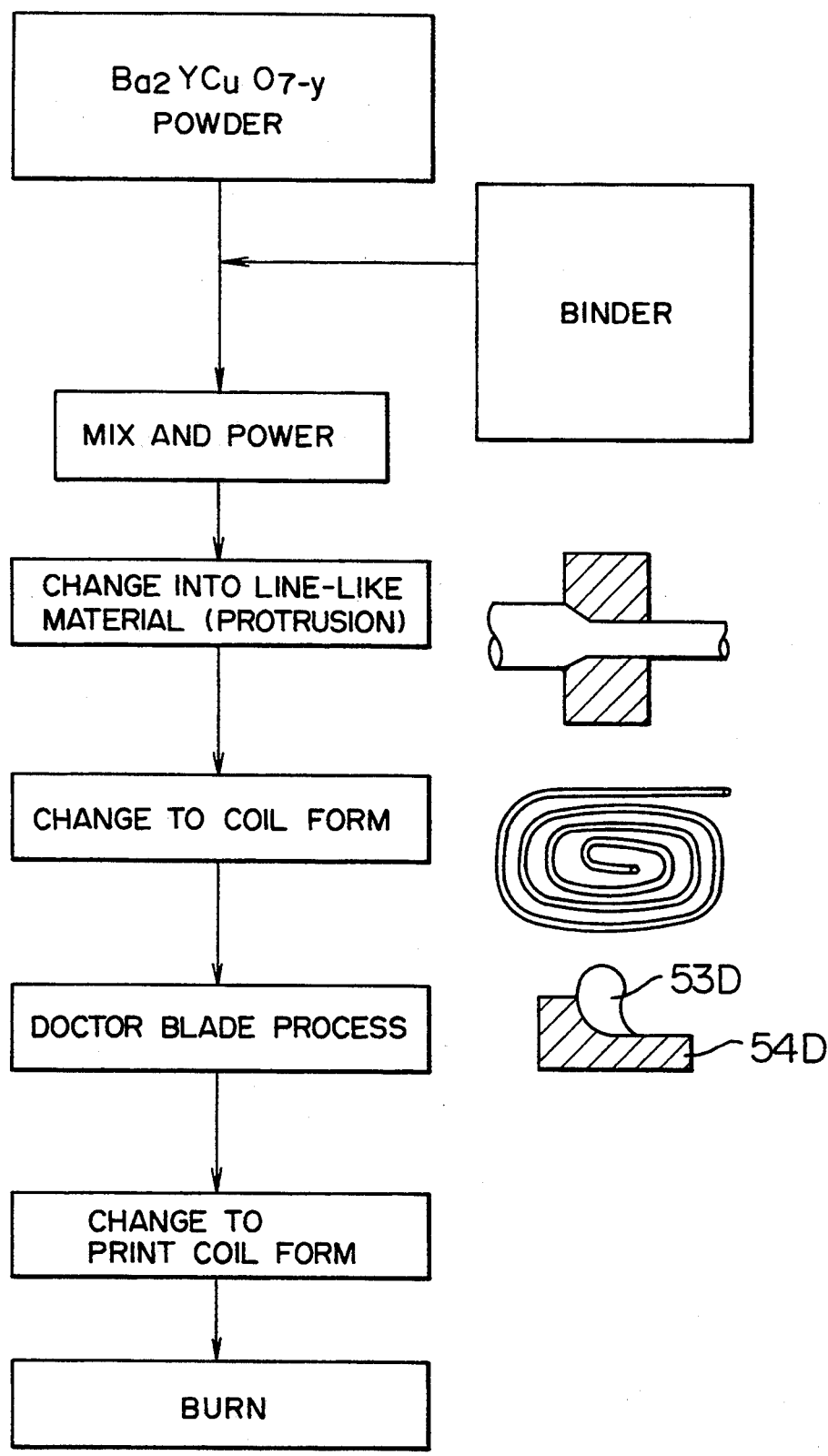
FIG. 16 is a block diagram of the manufacture of a thin film print coil as one embodiment of the fluxmeter according to the present invention.

FIG. 16 shows one example of the procedures of manufacturing a thin plate-like print coil. Oxides such as $Ba_2YCuO_{7-y}$ prepared beforehand are mixed with a binder and powdered. Generally an epoxy resin or epoxy resin organic binder is used as the binder. The compound is then changed into a strip-like material by cold working such as extrusion and then into a coil-like material. This material is then changed into a thin plate-like coil 54D by a doctor blade 53D. Finally, the binder is evaporated and the remaining powder is sintered by burning the thin plate-like coil 54D.

The doctor blade process will now be described. The doctor blade process includes the steps of uniformly mixing ceramic powder, a binder and a solvent; removing foams; adjusting the resulting mixture to provide a slurry; feeding this slurry onto a flat metal or glass plate; and adjusting the thickness of the slurry with a flat portion of a doctor blade by causing the blade to contact the flowing slurry. For example, if Bi superconductor is prepared, oxide materials are mixed at a composition ratio of $Bi_{0.7}Pb_{0.3}SrCaCu_{1.80_x}$ to prepare a high Tc phase Bi superconductor. This material is then powdered and mixed with an organic binder to prepare a slurry. This slurry is formed as a superconducting film on a substrate with a doctor blade to thereby form a print coil, which is then heat treated at a temperature, for example, of 500° C. for about one hour.

Figure 17A:
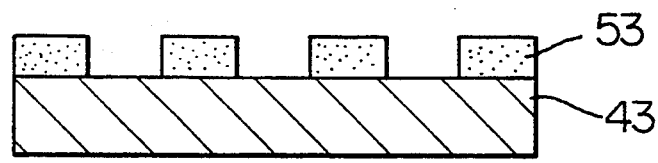
FIG. 17 illustrates one example of a method of manufacturing a thin film print coil of the fluxmeter according to the present invention.
Figure 17B:
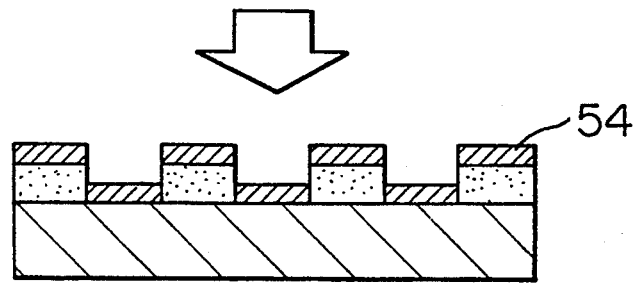
Figure 17C:
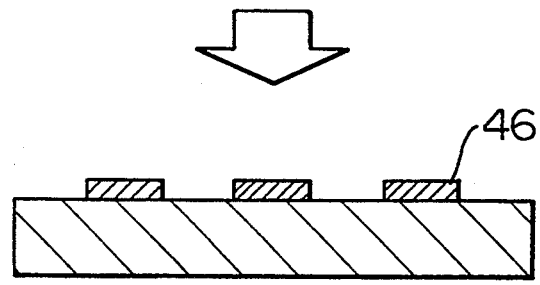
Figure 18A:
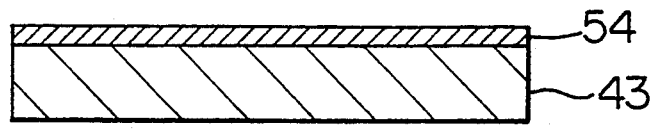
FIG. 18 illustrates another example of the method of manufacturing a thin film print coil of the fluxmeter according to the present invention.
Figure 18B:
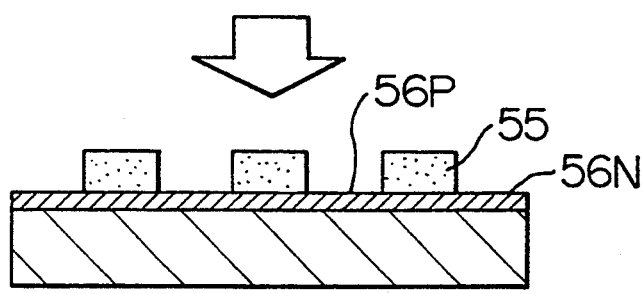
Figure 18C:
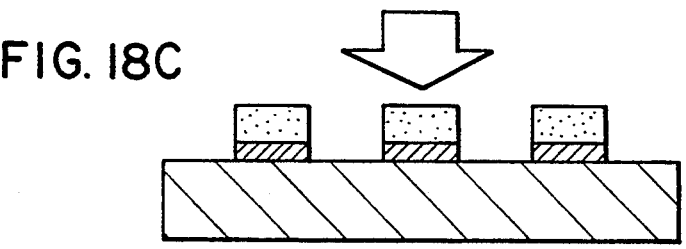
Figure 18D:
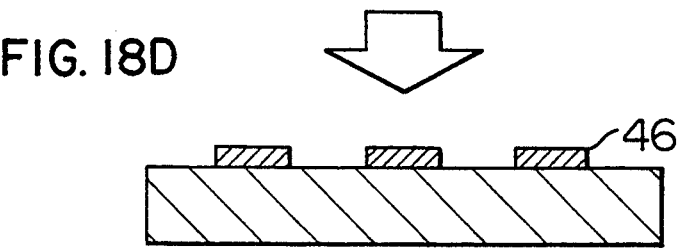

FIG. 17 illustrates the manufacture of a thin film-like print coil. A negative image of a print coil is formed on a substrate 43 with a photosensitive resin 53. Then a superconducting thin film 54 is deposited on the entire surface of the negative image. Areas having the photosensitive resin 53 and the thin film thereon are then removed with a solvent to thereby form with the remaining thin film a print coil 46.

The formation of a print coil with a Pb superconductor will be specifically described below as an example. A negative image of a print coil is formed on the substrate 43 with photosensitive resin 53. The substrate used is made of quartz glass or sapphire, and the photosensitive resin used is bisazide; N-acetyl 4 nitro 1 naphthylamine. A superconducting thin film 54 is then formed on the entire surface of the negative image. The superconductor used in the thin film 54 is of a Pb system. The thin film forming process is by vacuum deposition using resistance heating. The Pb thin film has low resistance to thermal distortion, and low waterproofness, so that Au and In are added in addition to Pb. Actually, Au (about 4% by weight), In (about 5–14% by weight) and Pb (about 82–88% by weight) are vacuum deposited sequentially in this order.

The solvent used may be an alkali solution or alcohol. The materials used in the above description are only as an example and other materials may be used in the present invention.

FIG. 18 illustrates a similar example of manufacturing a thin film print coil. A superconducting thin film 54 is formed on substrate 43. A positive pattern 56P of a print coil is formed with photosensitive resin 55. A negative pattern 56N is chemically etched away. The photosensitive resin 55 remaining on the positive pattern 56P is dissolved and removed with a solvent, and thus a thin film print coil 46 is formed.

The print coils of FIGS. 3 and 4 have intersections, the shape and making process of which will now be described by taking a print coil of FIG. 4 as an example.

Figure 29:
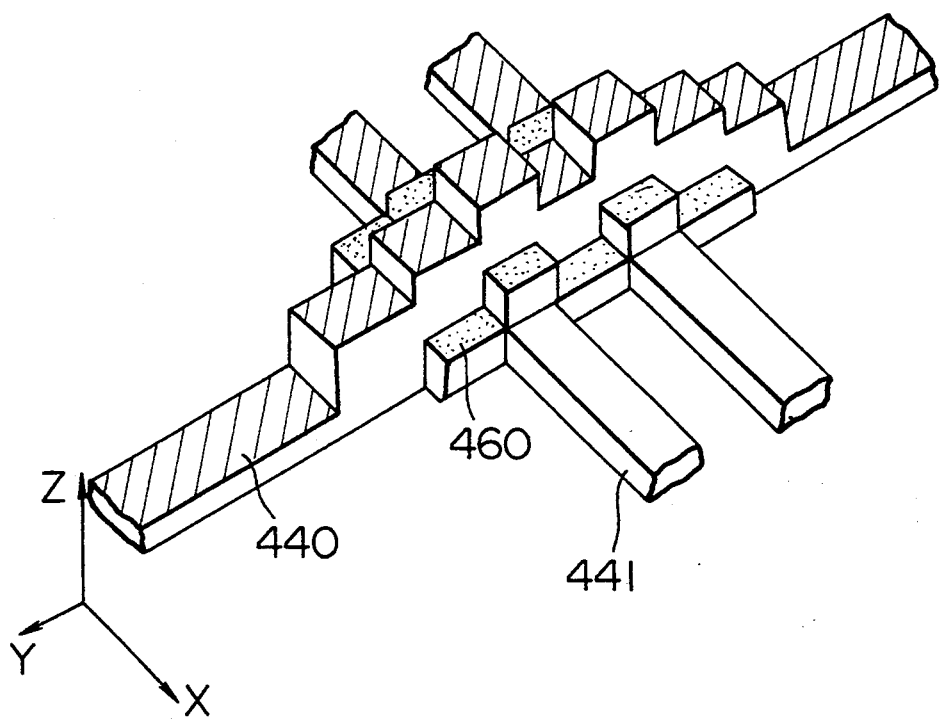
FIG. 29 schematically illustrates an intersection of the print coil of the fluxmeter according to the present invention.

FIG. 28 schematically illustrates the process of making the intersection of the superconducting print coil of FIG. 4. FIG. 29 schematically illustrates the intersection of the coil. In FIG. 28, Nb which becomes superconducted at 9.5 K is deposited on a glass substrate 430 at a growth rate of 2000 (Å/min) for 50 minutes by electron beam deposition (6 KW) to form an Nb superconducting film 440 of a thickness of 10 μm to thereby form a print coil. A mask 450 is placed on the thus formed film 440, a $SiO_2$ or LiF insulating film 460 about 15 μm thick is formed by sputtering from above. Care must be taken such that the insulating film should not be locally thinned (thick tens of angstroms) in order to avoid the formation of a Josephson junction. The mask 450 is then removed and a mask 451 is placed as shown. A Nb film is deposited 20 μm thick from above by electron beam deposition (6 KW). The mask 451 is then removed and thus an intersection as shown in FIG. 29 is formed. It is to be noted that when the insulating film 460 is extended longer than the superconducting film 440 in the X direction, the superconducting films 440 and 441 should not form a bridge and hence a Josephson junction therebetween.

Figure 30:
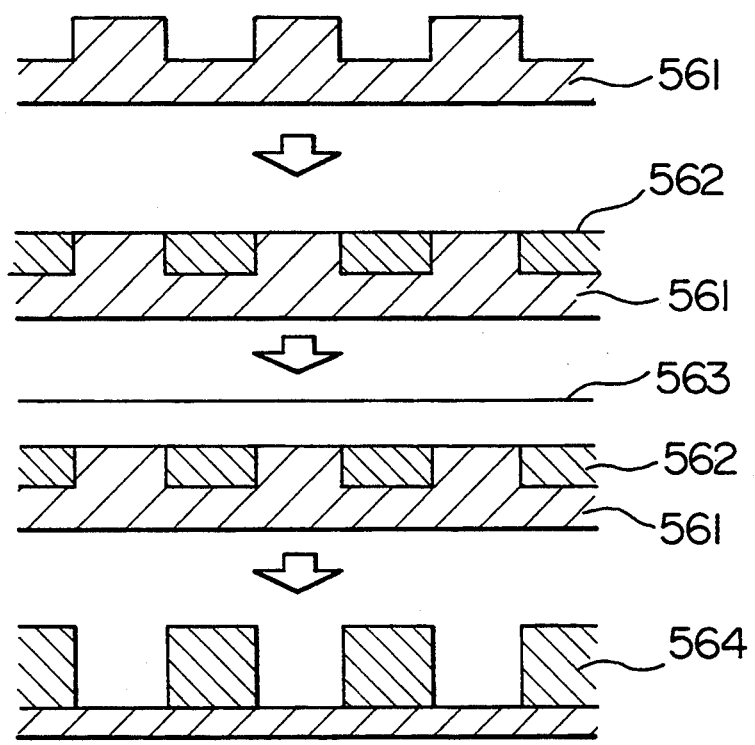
FIG. 30 illustrates one example of a method of manufacturing the print coil of the fluxmeter according to the present invention.

In addition, a process of manufacturing a superconducting print coil will be described. FIG. 30 shows another embodiment of the process of manufacturing a superconducting print coil. A Ti circuit pattern 562 is fitted in a groove configuration in an Nb substrate 561. The groove corresponds to a negative circuit pattern. A Cu—Sn alloy metal plate 563 is superimposed on and joined to the Ti-fitted substrate to thereby form a laminate of the substrate and alloy plate with the Ti being held therebetween. A laser beam is irradiated onto the laminate along the Ti pattern to cause a diffusion reaction between Nb and Sn both in the substrates to diffuse Ti to thereby form an $Nb_3Sn$—Ti superconducting circuit 564. The ambient $NiB_3Sn$ layer outside the pattern is removed by chemical means (etching) or a cutting process.

FIG. 31 illustrates another embodiment of the process of manufacturing a Y—Ba—Cu—O superconducting print coil. First, an ingot 565 of Y—Ba—Cu 3 element alloy is rolled to form a substrate 566. A polymer shielding sheet 567, for example of polyimide, in which a circuit pattern is stamped out is adhered to the substrate. The resulting intermediate is immersed in an aqueous alkali solution, for example of NaOH, while supplying the solution with an electric current to form an oxide layer 567 in the stamped groove (exposed substrate portions) in the sheet due to annodic oxidation. The substrate is then heated, for example, at 800°–950° C. for 5–100 hours. By this treatment, the oxygen in the oxide layer diffuses into the substrate and reacts with the respective associated elements and the respective elements in the substrate diffuse into the oxide layer and react with the oxygen to thereby form an oxide superconducting coil 568 ($YiBa_2Cu_3O_{4-x}$). Unnecessary portions may be chemically etched away or mechanically removed.

Figure 19:
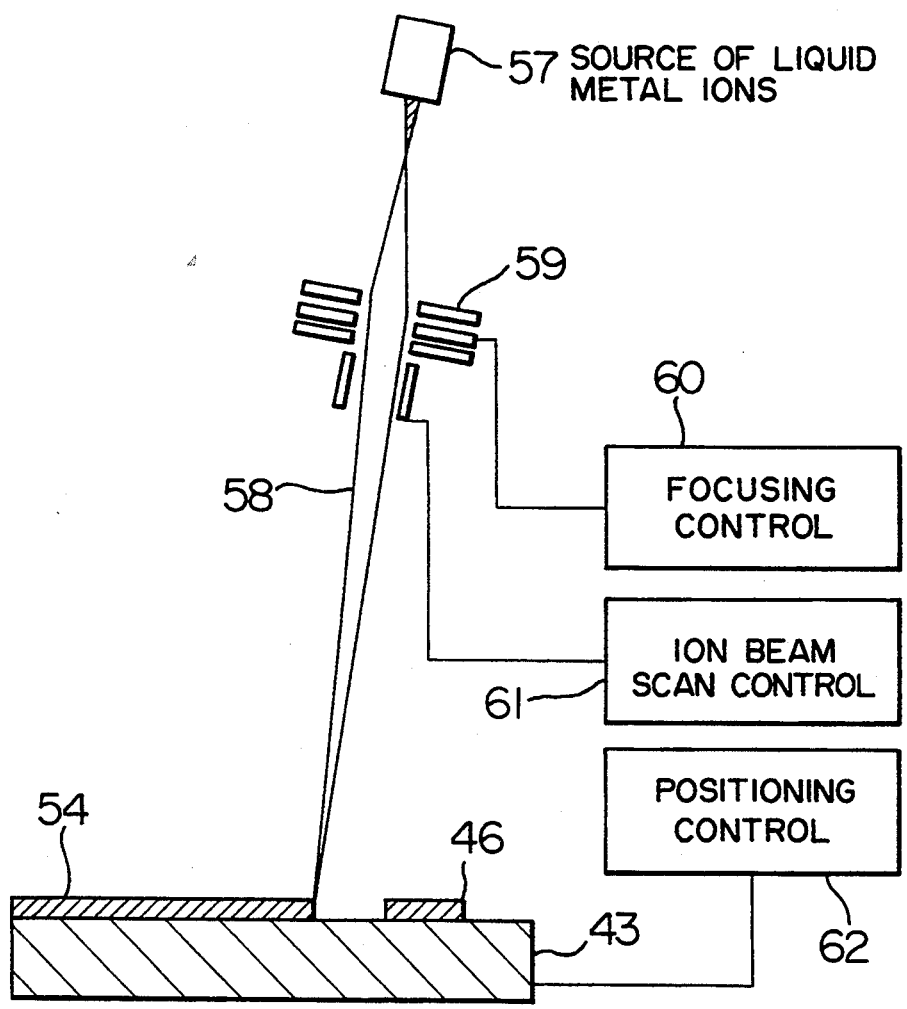
FIG. 19 illustrates the use of a focused ion beam as one example of a method of manufacturing a thin film print coil of the fluxmeter according to the present invention.

FIG. 19 illustrates one embodiment of a process of manufacturing a thin film print coil. A superconducting thin film 54 is formed on the substrate 43. The thin film is irradiated with a focused ion beam 58 from a source of liquid metal ions 57 for sputtering purposes. The focused ion beam 58 is controlled by an Einzel lens 59 via a focusing control 60 in conjunction with an ion beam scan control unit 61 and a substrate positioning control unit 62 to thereby form a thin film print coil 46. There are other various embodiments of the process. For example, a superconducting material $YBa_2Cu_3O_{7-\sigma}$ on a glass, quartz or YSZ (yttria stabilized zirconia) substrate can be worked using Ga or Au as a source of liquid metal ions. Of course, other suitable materials may be used. According to the embodiments of the present invention, a print coil can be manufactured advantageously without increasing the number of steps of manufacturing conventional superconducting thin films and line-like materials.

In the illustrated manufacture of the thin film print coil, if a high-permeability material which does not cause a phase separation when it is used as the substrate is used as a substrate for manufacturing the print coil, the formed coil can be used advantageously as a coil without being removed from the substrate. In addition, if a thin substrate generally low in permeability is used, it can be used advantageously as a member to define the distance between the print coil and a sample to be measured.

According to the present invention, the flux transmissibility of the flux transformer and the sensitivity and signal resolution of the flux meter are improved in the magnetic sensor comprising a superconducting quantum interferometer and flux transformer. Therefore, the degree of deterioration of ferrite stainless steel used under high-temperature environments such as chemical plants and nuclear plants can be sensed with high accuracy.

We claim:

1. A fluxmeter comprising:
   means for applying a magnetic field to an element of a plant;
   a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and
   a flux transmitting circuit including:
   a pickup coil opposingly arranged with said element of a plant for detecting a magnetic flux generated at said element of a plant by said means for applying a magnetic field,
   a second coil, connected to said pickup coil through a plurality of leads, for transmitting a signal indicative of said magnetic flux detected by said pickup coil to said superconducting quantum interference element by magnetic coupling,
   wherein said pickup coil includes a core for guiding said magnet flux generated at said element of a plant to increase an intensity of said signal indicative of said magnetic flux detected by said pickup coil;
   wherein said pickup coil is disposed at a distance ranging from 100 $\mu$m to 5 mm from said element of a plant; and
   wherein said pickup coil includes a print coil made of a superconducting material.

2. A fluxmeter according to claim 1, wherein the pickup coil is formed by sputtering.

3. A fluxmeter according to claim 1, wherein the pickup coil is formed by laser sputtering deposition.

4. A fluxmeter according to claim 1, wherein the pickup coil is formed by MBE deposition.

5. A fluxmeter according to claim 1, wherein the pickup coil is formed by MOCVD.

6. A fluxmeter according to claim 1, wherein the pickup coil is formed by spray pyrolysis deposition.

7. A fluxmeter according to claim 1, further comprising:
   means disposed between said pickup coil and said element of a plant for defining a distance between the element of a plant and said pickup coil.

8. A flux meter comprising:
   means for applying a magnetic field to an element of a plant;
   a superconducting quantum interference element for measuring a change in at least one magnetic characteristic selected from a group of magnetic characteristics of said element of a plant, said group of magnetic characteristics includes a residual flux density a coercive force, a magnetic hysteresis loop area and a magnetic hysteresis figure; and
   a flux transmitting circuit including:
   a pickup coil opposingly arranged with said element of a plant for detecting a magnetic flux generated at said element of a plant by said means for applying a magnetic field,
   a second coil, connected to said pickup coil through a plurality of leads, for transmitting a signal indicative of said magnetic flux detected by said pickup coil to said superconducting quantum interference element by magnetic coupling,
   wherein said pickup coil includes a core for guiding said magnetic flux generated at said element of a plant to increase an intensity of said signal indicative of said magnetic flux detected by said pickup coil.

9. A fluxmeter according to claim 8 further comprising:
   means disposed between said pickup coil and said element of a plant for defining a distance between the element of a plant and said pickup coil.

10. A fluxmeter according to claim 9, wherein said distance is 100 $\mu$m–5 mm.

11. A fluxmeter according to claim 8, wherein the flux transmitting circuit further; includes two pickup coils connected in series and disposed so as to cancel magnetic flux from each other.

12. A fluxmeter according to claim 8, further comprising:
   a magnetic shielding plate for magnetically shielding the superconducting quantum interference element, the plurality of leads of the flux transmitting circuit and said second coil.

13. A fluxmeter according to claim 8, further comprising:
   a magnetic shielding plate for magnetically shielding the whole fluxmeter except on a side thereof which receives the magnetic flux from the element of a plant.

14. A fluxmeter according to claim 8, further comprising:
   a magnetic shielding plate for magnetically shielding the whole fluxmeter except on a side where said pickup coil is located.

15. A fluxmeter according to claim 8, wherein said pickup coil is formed in a spiral shape and said core is surrounded by a conducting line of said pickup coil formed in spiral shape.

16. A fluxmeter according to claim 8, wherein said core includes a portion which is disposed closer to said element of a plant than said pickup coil.

17. A fluxmeter comprising:
   means for applying a magnetic field to an element of a plant;
   a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and
   flux transmitting circuit including:
   a pickup coil opposingly arranged with said element of a plant for detecting a magnetic flux generated at said element of a plant by said means for applying a magnetic field,
   a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil;

wherein said pickup coil is disposed at a distance ranging from 100 μm to 5 mm from said element of a plant.

18. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil.

19. A fluxmeter comprising:

application means for applying a magnetic field to an element of a plant;

a pickup coil opposingly arranged with said element of a plant for detecting a magnetic flux generated at said element of a plant by said application means for applying a magnetic field;

a core, provided with said pickup coil, a portion of said core disposed closer to said element of a plant than said pickup coil, for guiding said magnetic flux generated at said element of a plant to increase an intensity of a signal indicative of said magnetic flux detected by said pickup coil;

a second coil, connected to said pickup coil through a plurality of leads, for transmitting said signal indicative of said magnetic flux detected by said pickup coil;

a superconducting quantum interference element for measuring, from said signal indicative of said magnetic flux transmitted from said second coil by magnetic coupling, at least one magnetic characteristic selected from a group of magnetic characteristics of said element of a plant, said group of magnetic characteristics includes a residual flux density, a coercive force, a magnetic hysteresis loop area and a magnetic hysteresis figure;

storage means for storing data regarding at least said magnetic characteristic of said element of a plant in a virgin unused state or a material in a virgin unused state constituting an element of a plant; and determination means for determining degree of deterioration of said element of a plant by comparing at least said magnetic characteristic of said element of a plant measured by said superconducting quantum interference element to said data regarding said element of a plant or said material in a virgin state.

20. A method of sensing the degree of deterioration of an element of a plant to be measured, comprising the steps of:

applying a magnetic field across an element of a plant to be measured;

measuring a change in at least one magnetic characteristic selected from a group of magnetic characteristics of said element of a plant, said group of magnetic characteristics including a residual flux density, a coercive force, a magnetic hysteresis loop area and a magnetic hysteresis loop figure, by using a fluxmeter;

said fluxmeter including:

a superconducting quantum interference element for measuring a change in said at least one magnetic characteristic of said element of a plant to be measured; and a flux transmitting circuit having a pickup coil opposingly arranged with said element of a plant for detecting a magnetic flux generated at said element of a plant by said applying step, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnetic flux generated at said element of a plant to increase an intensity of said signal indicative of said magnetic flux detected by said pickup coil; and determining degree of deterioration of the element of a plant from the measured change in said at least one magnetic characteristic.

21. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnet flux generated at said object to increase an intensity of said signal indicative of said magnetic flux detected by said pickup coil;

wherein said pickup coil is disposed at a distance ranging from 100 μm to 5 mm from said element of a plant; and wherein said pickup coil includes a print coil made of a superconducting material by powdering and mixing a mixture of a superconducting material and a binder, cold working the mixture to form a line-like material, working the line-like material into a coil-like material, working the coil-like material into a print coil-like material in a doctor blade process and sintering the print coil-like material.

22. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnet flux generated at said element of a plant to increase an intensity of said signal indicative of said magnetic flux detected by said pickup coil.;

wherein said pickup coil is disposed at a distance ranging from 100 μm to 5 mm from said element of a plant; and wherein said pickup coil includes a print coil made of a superconducting material by forming a thin film negative pattern of a print coil with a photosensitive resin on a substrate, depositing a superconducting thin film on the entire surface of the substrate with the negative pattern thin film, removing the thin film constituting the negative pattern and the superconducting thin film using a solvent.

23. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnet flux generated at said element of a plant to increase an intensity of said signal indicative of said magnetic flux detected by said pickup coil;

wherein said pickup coil is disposed at a distance ranging from 100 μm to 5 mm from said element of a plant; and wherein said pickup coil includes a print coil made of a superconducting material by forming a superconducting thin film on a substrate, forming a positive pattern of a print coil on the superconducting thin film with a photosensitive resin, etching away a negative pattern portion of the superconducting thin film, and removing with a solvent the photosensitive resin remaining on the positive pattern.

24. A flux meter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnetic flux generated at said element of a plant to increase an intensity of said signal indicative of said magnetic flux detected by said pickup coil and a print coil made of a superconducting material by powdering and mixing a mixture of a superconducting material and a binder, cold working the mixture to form a line-like material, working the line-like material into a coil-like material, working the coil-like material into a print coil-like material in a doctor blade process and sintering the print coil-like material.

25. A flux meter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density a coercive force, a magnetic hysteresis loop area and a magnetic hysteresis figure; and a flux transmitting circuit including:

a pickup coil opposingly arranged with said object for detecting a magnetic flux generated at said object by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnetic flux generated at said object to increase an intensity of said signal indicative of said magnetic flux detected by said pickup coil and a print coil made of a superconducting material by forming a thin film negative pattern of a print coil with a photosensitive resin on a substrate, depositing a superconducting thin film on the entire surface of the substrate with the negative pattern thin film, removing the thin film constituting the negative pattern and the superconducting thin film using a solvent.

26. A flux meter comprising:

means for applying a magnetic field to an object; a superconducting quantum interference element for measuring a change in at least one magnetic characteristic selected from a group of magnetic characteristics of said object, said group of magnetic characteristics includes a residual flux density a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnetic flux generated at said element of a plant to increase an intensity of said signal indicative of said magnetic flux detected by said pickup coil and a print coil made of a superconducting material by forming a superconducting thin film on a substrate, forming a positive pattern of a print coil on the superconducting thin film with a photosensitive resin, etching away a negative pattern portion of the superconducting thin film and removing with a solvent the photosensitive resin remaining on the positive pattern.

27. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil;

wherein said pickup coil is disposed at a distance ranging from 100 μm to 5 mm from said element of a plant; and wherein said pickup coil includes a print coil made of a superconducting material by powdering and mixing a mixture of a superconducting material and a binder, cold working the mixture to form a line-like material, working the line-like material into a coil-like material, working the coil-like material into a print coil-like material in a doctor blade process and sintering the print coil-like material.

28. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil;

wherein said pickup coil is disposed at a distance ranging from 100 μm to 5 mm from said element of a plant; and wherein said pickup coil includes a print coil made of a superconducting material by forming a thin film negative pattern of a print coil with a photosensitive resin on a substrate, depositing a superconducting thin film on the entire surface of the substrate with the negative pattern thin film, removing the thin film constituting the negative pattern and the superconducting thin film using a solvent.

29. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil;

wherein said pickup coil is disposed at a distance ranging from 100 μm to 5 mm from said element of a plant; and wherein said pickup coil includes a print coil made of a superconducting material by forming a superconducting thin film on a substrate, forming a positive pattern of a print coil on the superconducting thin film with a photosensitive resin, etching away a negative pattern portion of the superconducting thin film and removing with a solvent the photosensitive resin remaining on the positive pattern.

30. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil and a print coil made of a superconducting material by powdering and mixing a mixture of a superconducting material and a binder, cold working the mixture to form a line-like material, working the line-like material into a coil-like material, working the coil-like material into a print coil-like material in a doctor blade process and sintering the print coil-like material.

31. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil and a print coil made of a superconducting material by forming a thin film negative pattern of a print coil with a photosensitive resin on a substrate, depositing a superconducting thin film on the entire surface of the substrate with the negative pattern thin film, removing the thin film constituting the negative pattern and the superconducting thin film using a solvent.

32. A fluxmeter comprising:

means for applying a magnetic field to an element of a plant;

a superconducting quantum interference element for measuring a change in at least one magnetic characteristic selected from a group of magnetic characteristics of said element of a plant, said group of magnetic characteristics includes a residual flux density, a coercive force, a magnetic hysteresis loop area and a magnetic hysteresis figure; and a flux transmitting circuit including:

a pickup coil opposingly arranged with said element of a plant for detecting a magnetic flux generated at said element of a plant by said means for applying a magnetic field, a second coil, connected to said pickup coil through a plurality of leads, for transmitting a signal indicative of said magnetic flux detected by said pickup coil to said superconducting quantum interference element by magnetic coupling, wherein said pickup coil includes a core, a portion of which is disposed closer to said element of a plant than said pickup coil, for guiding said magnetic flux generated at said element of a plant so as to increase an intensity of said signal indicative of said magnetic flux detected by said pickup coil and a print coil made of a superconducting material by forming a superconducting thin film on a substrate, forming a positive pattern of a print coil on the superconducting thin film with a photosensitive resin, etching away a negative pattern portion of the superconducting thin film and removing with a solvent the photosensitive resin remaining on the positive pattern.

33. A fluxmeter comprising:

application means for applying a magnetic field to an element of a plant;

a pickup coil opposingly arranged with said element of a plant for detecting a magnetic flux generated at said element of a plant by said application means for applying a magnetic field;

a core, provided with said pickup coil, a portion of said core disposed closer to said element of a plant than said pickup coil, for guiding said magnetic flux generated at said element of a plant to increase an intensity of a signal indicative of said magnetic flux detected by said pickup coil;

a second coil, connected to said pickup coil through a plurality of leads, for transmitting said signal indicative of said magnetic flux detected by said pickup coil;

a superconducting quantum interference element for measuring, from said signal indicative of said magnetic flux transmitted from said second coil by magnetic coupling, at least one magnetic characteristic selected from a group of magnetic characteristics of said element of a plant, said group of magnetic characteristics includes a residual flux density, a coercive force, a magnetic hysteresis loop area and a magnetic hysteresis figure;

storage means for storing data regarding at least said magnetic characteristic of said element of a plant in a virgin unused state or a material in a virgin unused state constituting said element of a plant; and determination means for determining degree of deterioration of said element of a plant by comparing at least said magnetic characteristic of said element of a plant measured by said superconducting quantum interference element to said data regarding said element of a plant or said material in a virgin state;

wherein said pickup coil includes a print coil made of a superconducting material by powdering and mixing a mixture of a superconducting material and a binder, cold working the mixture to form a line-like material, working the line-like material into a coil-like material, working the coil-like material into a print coil-like material in a doctor blade process, and sintering the print coil-like material.

34. A fluxmeter comprising:

application means for applying a magnetic field to an element of a plant;

a pickup coil opposingly arranged with said element of a plant for detecting a magnetic flux generated at said element of a plant by said application means for applying a magnetic field;

a core, provided with said pickup coil, a portion of said core disposed closer to said element of a plant than said pickup coil, for guiding said magnetic flux generated at said element of a plant to increase an intensity of a signal indicative of said magnetic flux detected by said pickup coil;

a second coil, connected to said pickup coil through a plurality of leads, for transmitting said signal indicative of said magnetic flux detected by said pickup coil;

a superconducting quantum interference element for measuring, from said signal indicative of said magnetic flux transmitted from said second coil by magnetic coupling, at least one magnetic characteristic selected from a group of magnetic characteristics of said element of a plant, said group of magnetic characteristics includes a residual flux density, a coercive force, a magnetic hysteresis loop area and a magnetic hysteresis figure;

storage means for storing data regarding at least said magnetic characteristic of said element of a plant in a virgin unused state or a material in a virgin unused state constituting said element of a plant; and determination means for determining degree of deterioration of said element of a plant by comparing at least said magnetic characteristic of said element of a plant measured by said superconducting quantum interference element to said data regarding said element of a plant or said material in a virgin state;

wherein said pickup coil includes a print coil made of a superconducting material by forming a thin film negative pattern of a print coil with a photosensitive resin on a substrate, depositing a superconducting thin film on the entire surface of the substrate with the negative pattern thin film, removing the thin film constituting the negative pattern and the superconducting thin film using a solvent.

35. A fluxmeter comprising:

application means for applying a magnetic field to an element of a plant;

a pickup coil opposingly arranged with said element of a plant for detecting a magnetic flux generated at said element of a plant by said application means for applying a magnetic field;

a core, provided with said pickup coil, a portion of said core disposed closer to said element of a plant than said pickup coil, for guiding said magnetic flux generated at said element of a plant to increase an intensity of a signal indicative of said magnetic flux detected by said pickup coil;

a second coil, connected to said pickup coil through a plurality of leads, for transmitting said signal indicative of said magnetic flux detected by said pickup coil;

a superconducting quantum interference element for measuring, from said signal indicative of said magnetic flux transmitted from said second coil by magnetic coupling, at least one magnetic characteristic selected from a group of magnetic characteristics of said element of a plant, said group of magnetic characteristics includes a residual flux density, a coercive force, a magnetic hysteresis loop area and a magnetic hysteresis figure;

storage means for storing data regarding at least said magnetic characteristic of said element of a plant in a virgin unused state or a material in a virgin unused state constituting said element of a plant; and determination means for determining degree of deterioration of said element of a plant by comparing at least said magnetic characteristic of said element of a plant measured by said superconducting quantum interference element to said data regarding said element of a plant or said material in a virgin state;

wherein said pickup coil includes a print coil made of a superconducting material by forming a superconducting thin film on a substrate, forming a positive pattern of a print coil on the superconducting thin film with a photosensitive resin, etching away a negative pattern portion of the superconducting thin film; and removing with a solvent the photosensitive resin remaining on the positive pattern.

36. A method of sensing the degree of deterioration of an element of a plant to be measured, comprising the steps of:

applying a magnetic field across an element of a plant to be measured;

measuring a change in at least one magnetic characteristic selected from a group of magnetic characteristics of said element of a plant, said group of magnetic characteristics including a residual flux density, a coercive force, a magnetic hysteresis loop area and a magnetic hysteresis loop figure, by using a fluxmeter;

said fluxmeter including:

a superconducting quantum interference element for measuring a change in said at least one magnetic characteristic of said element of a plant to be measured; and a flux transmitting circuit having a pickup coil opposingly arranged with said element of a plant for detecting a magnetic flux generated at said element of a plant by said applying step, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnetic flux generated at said element of a plant to increase an intensity of said signal indicative of said magnetic flux detected by said pickup coil and a print coil made of a superconducting material by powdering and mixing a mixture of a superconducting material and a binder, cold working the mixture to form a line-like material, working the line-like material into a coil-like material, working the coil-like material into a print coil-like material in a doctor blade process; and sintering the print coil-like material; and determining degree of deterioration of the element of a plant from the measured change in said at least one magnetic characteristic.

37. A method of sensing the degree of deterioration of an element of a plant to be measured, comprising the steps of:

applying a magnetic field across an element of a plant to be measured;

measuring a change in at least one magnetic characteristic selected from a group of magnetic characteristics of said element of a plant, said group of magnetic characteristics including a residual flux density, a coercive force, a magnetic hysteresis loop area and a magnetic hysteresis loop figure, by using a fluxmeter;

said fluxmeter including:

a superconducting quantum interference element for measuring a change in said at least one magnetic characteristic of said element of a plant to be measured; and a flux transmitting circuit having a pickup coil opposingly arranged with said element of a plant for detecting a magnetic flux generated at said element of a plant by said applying step, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnetic flux generated at said element of a plant to increase an intensity of said signal indicative of said magnetic flux detected by said pickup coil and a print coil made of a superconducting material by forming a thin film negative pattern of a print coil with a photosensitive resin on a substrate, depositing a superconducting thin film on the entire surface of the substrate with the negative pattern thin film, removing the thin film constituting the negative pattern and the superconducting thin film using a solvent; and determining degree of deterioration of the element of a plant from the measured change in said at least one magnetic characteristic.

38. A method of sensing the degree of deterioration of an element of a plant to be measured, comprising the steps of:

applying a magnetic field across an element of a plant to be measured;

measuring a change in at least one magnetic characteristic selected from a group of magnetic characteristics of said element of a plant, said group of magnetic characteristics including a residual flux density, a coercive force, a magnetic hysteresis loop area and a magnetic hysteresis loop figure, by using a fluxmeter;

said fluxmeter including:

a superconducting quantum interference element for measuring a change in said at least one magnetic characteristic of said element of a plant to be measured; and a flux transmitting circuit having a pickup coil opposingly arranged with said element of a plant for detecting a magnetic flux generated at said element of a plant by said applying step, a second coil, connected to said pickup coil through a plurality of leads, for transmitting a signal indicative of said magnetic flux detected by said pickup coil to said superconducting quantum interference element by magnetic coupling, wherein said pickup coil includes a core for guiding said magnetic flux generated at said element of a plant to increase an intensity of said signal indicative of said magnetic flux detected by said pickup coil and a print coil made of a superconducting material by forming a superconducting thin film on a substrate, forming a positive pattern of a print coil on the superconducting thin film with a photosensitive resin, etching away a negative pattern portion of the superconducting thin film; and removing with a solvent the photosensitive resin remaining on the positive pattern; and determining degree of deterioration of the element of a plant from the measured change in said at least one magnetic characteristic.

* * * * *